United States Patent [19]

Dunn et al.

[11] Patent Number: 5,071,965

[45] Date of Patent: Dec. 10, 1991

[54] NOVEL TC-99M COMPLEXES

[75] Inventors: T. Jeffrey Dunn, Cedar Mill; Dennis Nosco, Florissant; Steven Woulfe, Hazelwood, all of Mo.; Richard Dean, Downingtown, Pa.; Dennis Wester, Lynwood, Wash.

[73] Assignee: Mallinckrodt Medical, Inc., St. Louis, Mo.

[21] Appl. No.: 315,168

[22] Filed: Feb. 24, 1989

Related U.S. Application Data

[63] Continuation-in-part of Ser. No. 221,099, Jul. 19, 1988, abandoned.

[51] Int. Cl.$^5$ .............................................. C07F 13/00
[52] U.S. Cl. ........................................ 534/14; 424/1.1
[58] Field of Search ...................... 424/1.1; 534/10, 14

[56] References Cited

U.S. PATENT DOCUMENTS

| | | |
|---|---|---|
| 3,369,121 | 2/1968 | Bruno et al. |
| 3,466,361 | 9/1968 | Richards et al. |
| 3,720,761 | 3/1973 | Hunter, Jr. |
| 3,723,612 | 3/1973 | Mikheev et al. |
| 3,725,295 | 4/1973 | Eckelman et al. |
| 3,735,001 | 5/1973 | McRae et al. |
| 3,749,556 | 8/1971 | Barak et al. |
| 3,803,299 | 4/1974 | Nouel. |
| 3,863,004 | 1/1975 | Wolfangel. |
| 3,920,995 | 11/1975 | Czaplinski et al. |
| 4,795,626 | 1/1989 | Deutsch et al. ........................ 424/1.1 |

FOREIGN PATENT DOCUMENTS 9000854 2/1990 PCT Int'l Appl.

OTHER PUBLICATIONS

Green et al., Gallium-68, 1,1,1-Tris (5-Methoxysalicyaldiminomethyl) Ethane: A Potential Tracer for Evaluation of Regional Myocardial Blood Flow, *J. Nucl. Med.*, 26:170-180, 1985.
Deutsch et al., Technetium Chemistry and Technetium Radiopharmaceuticals, *Prog. Inorg. Chem.*, 30:75-139, (1983).
Green et al., Synthesis and Crystallographic Characterization of a Gallium Salyicylaldimine Complex of Radiopharmaceutical Interest, *J. Am. Chem. Soc.*, 106:3689, 1984.
Skarzewski et al., Lipophilic Complexones, Part 3—Synthesis of Polyamines Derived from 2-Alkyl-1,3-propanediols and 2,2-Bis(hydroxymethyl) alkanols, *Monatshefte fur Chemie*, 114:1071-1077, 1983.
Oehmke et al., Some Combination Compounds of the 2,2-Diaminomethyl-1,3-Diaminopropane Moiety, *J. Inorg. Nucl. Chem.*, 27:2199, (1965).
Smith et al., *Inorg. Chem.*, 27:3929-3934, (1988).

Primary Examiner—John S. Maples
Attorney, Agent, or Firm—Rothwell, Figg, Ernst & Kurz

[57] ABSTRACT

Complexes useful as radiopharmaceutical imaging agents comprise technetium bonded to a ligand which generally can be described by the formula:

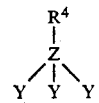

wherein
Z is N, C, B or P;
the three Y groups can be the same or different, each characterized by the general formula

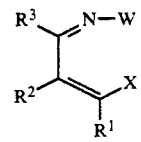

and $R^1$, $R^2$, $R^3$, $R^4$, W, and X are further defined herein.

1 Claim, No Drawings

NOVEL TC-99M COMPLEXES

This application is a continuation-in-part of Ser. No. 221,099, filed July 19, 1988, now abandoned.

BACKGROUND OF THE INVENTION

The present invention relates to ligands useful in forming complexes with radionuclide metal ions to provide materials useful for in vivo diagnostic and therapeutic applications. More specifically, the ligands of the present invention have particular application in the formation of complexes with technetium-99 m.

The use of radionuclide metal ions in therapeutic and in vivo diagnostic applications has been practiced for some time. For example, gamma-emitting radionuclide metal ions, including technetium-99 m, have been used in diagnostic scintigraphy for tumor detection. Beta-emitting isotopes, including rhenium-186, rhenium-188 and rhenium-189, can be used therapeutically in the treatment of tumors. Positron emission tomography may be used for diagnostic imaging and its use for evaluation of regional cerebral and myocardial blood flow is well documented.

Diagnostic nuclear medicine involves the administration to a subject of a radiation-emitting isotope which localizes in the tissues of interest. An image of these tissues then is obtained using a scintillation camera such as an Anger scintillation camera. Tc-99 m is an ideal radioisotope for use in nuclear medicine It has a half-life of 6 hours and a gamma-radiation of 140 keV, with no alpha or beta radiation. It is easily prepared using a Mo-99 m generator and is relatively inexpensive. Finally, its chemistry is such that it can be incorporated into diverse chemical forms in order to image different types of tissues.

Tc-99 m has become widely used for scintillation scanning of bone tissue and infarcted myocardial tissue. In these applications, the Tc-99 m is administered with a carrier such as methanehydroxydiphosphonate and a reducing agent such as $SnCl_2$. The Tc-99 m diphosphonate complex acts as a calcium-seeking agent which accumulates in bone, particularly at sites of high calcium turnover in newly forming or cancerous bone, and in myocardial infarcts that contain calcium phosphate.

Within the past several years, interest has developed in producing Tc-99 m-based radiodiagnostic agents which will accumulate in normal heart tissue, as opposed to infarcted tissue Such radiodiagnostic agents would be of great benefit inasmuch as they would allow for the early identification of individuals at high risk of having heart attacks.

The efficacy of radionuclides in in vivo diagnostic and therapeutic applications depends on the ability of the ligand-radionuclide complex to deliver the radionuclide to the site of the target cells. Thus, the biodistribution of these imaging compounds may determine their usefulness in various therapeutic or diagnostic applications.

There is a continuing need in the art for ligands which form stable complexes with known radionuclides, particularly, technetium, and which are useful in diagnostic and therapeutic imaging applications. There also is a need in the art for ligand-radionuclide complexes which display good biodistribution when utilized as diagnostic and therapeutic imaging agents.

The use of such ligands in technetium chemistry is more involved than with other radionuclides, such as In-111, Ga-67, Ga-68, Cu-67 and Tl-201. The chemistry of technetium involves a reduction of the starting Tc (VII) oxidation state that is inextricably coupled to the complexing of the reduced technetium with a ligand. For the other radionuclides only the complexing step is necessary as they are provided in the desired oxidation state. This fact makes the chemistry of technetium unique. Because of these differences, it is difficult to predict which of the ligands that can form complexes with indium-111, gallium-67 or -68, or copper -67 also can form complexes with technetium-99 m to provide useful radiodiagnostic agents.

Green, et al., *J. Nuclear Med.*, 26:170-180 (1985), teaches the reaction of tris (acetylacetonato) gallium (III) with 1, 1, 1-tris (5-methoxysalicyl-aldiminomethyl) ethane to produce a neutral six coordinate complex. The gallium complex was tested for its ability as an imaging agent in positron emission tomography. This complex has no overall charge. The images of a dog's heart and the biodistribution data in rats from the compound showed that the compound washed out quickly from the heart, indicative of its neutral character. No further mention of this or other derivatives of this ligand with gallium for use in nuclear medicine have been found in the literature.

It is an object of this invention to provide novel complexes of ligands with technetium which are useful as radiodiagnostic agents. More specifically, it is an object of this invention to provide such complexes which are useful as heart imaging agents. Further objects of the invention will become apparent upon reading the description of the invention and appended claims set forth below.

SUMMARY OF THE INVENTION

Complexes of the present invention are useful as radiopharmaceutical imaging agents and comprise technetium bonded to a ligand which generally can be described by the formula:

wherein

Z is N, C, B or P;

$R^4$ is H, R, hydroxy,

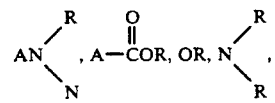

$ANA-O-C-R$,

A—O—ACN, an alicyclic ring,

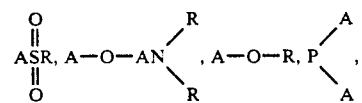

a fatty acid residue, an aryl group substituted with F, NO$_2$ or

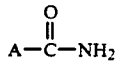

or aryloxy substituted with F, NO$_2$ or

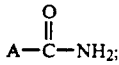

provided, however, when Z is N or P, R$^4$ is not present; and the three Y groups can be the same or different, each characterized by the general formula

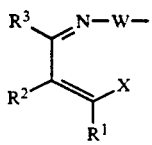

wherein

W is Q or O, provided, however that when W is O, Z is B or when Z is B, W is O;

X is OH, NH$_2$, NC, SH,

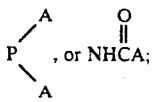

R$^3$ is H, R, SR,

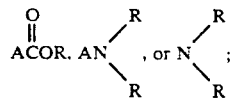

R$^1$ and R$^2$, independently, are A, SA, O—A,

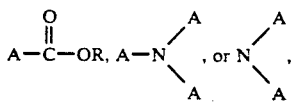

or R$^1$ and R$^2$, when taken together with the carbon atoms to which they are directly attached, can form an aryl group such that Y has the general formula

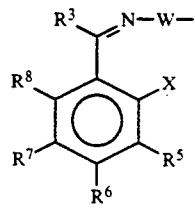

wherein

W, X and R$^3$ are as defined above, and

R$^5$, R$^6$, R$^7$ and R$^8$, independently, are H, OH, R, CO$_2$R,

NO$_2$, F, Cl, Br, I, CF$_3$,

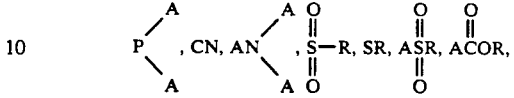

or NA$_3$—I—, or R$^7$ and R$^8$, when taken together with the carbon atoms to which they are directly attached, can form an aryl group having 6 to 10 carbon atoms;

Q is a branched or unbranched, saturated or unsaturated alkyl group having from 1 to 4 carbon atoms;

A is a branched or unbranched, saturated or unsaturated alkyl group having from 1 to 10 carbon atoms and R is a branched or unbranched, unsaturated or saturated alkyl, alkoxy, alkoxyalkyl, acyl, alkylacyl, alkoxyacyl, hydroxyalkyl, hydroxyalkylamine, alkylamide, alkylamine, acylamine or acylalkylamine wherein each alkyl or acyl portion has 1 to 10 carbon atoms, or R is an aryl group which can be further substituted with one or more alkoxy or saturated or unsaturated alkyl groups each having 1 to 10 carbon atoms or with an aryl or aryloxy group having 6 to 10 carbon atoms.

In certain preferred embodiments of the invention, in the ligand portion of the complex, Z is C, X is OH and W is CH$_2$. Especially useful complexes are those in which the ligand portion of the complex is (5-methylsal)$_3$tame, (4,6-dimethoxysal)$_3$tame, (4-methoxysal)-$_3$tame or (sal)$_3$tame O-n-propyl.

DETAILED DESCRIPTION OF THE PREFERRED EMBODIMENTS

In accordance with the present invention, there are disclosed novel complexes of technetium useful as radiodiagnostic agents. Each complex comprises Tc-99 m, having a +3 or +4 oxidation state, complexed with a compound referred to herein as a (Sal)$_3$tame. The complexes are formed by reaction of a technetium precursor and a (Sal)$_3$tame or reduced (Sal)$_3$tame compound in the presence of a reductant.

Specifically, the complexes of this invention comprise technetium bonded to a ligand of the general formula:

wherein

Z is N, C, B or P;

R$^4$ is H, R, hydroxy,

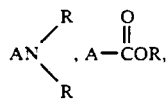

OR,

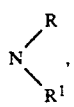

AOH, ANA$_3$+, ANA—O—R,

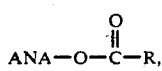

A—O—ACN, an alicyclic ring,

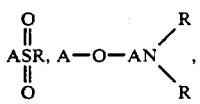

A—O—R,

a fatty acid residue, an aryl group substituted with F, NO$_2$ or

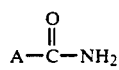

or aryloxy substituted with
F, NO$_2$ or

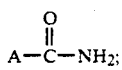

provided, however, when Z is N or P, R$^4$ is not present, and the three Y groups can be the same or different, each characterized by the general formula

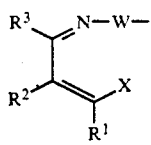

wherein
W is Q or O, provided, however that when W is O, Z is B or when Z is B, W is O;
X is OH, NH$_2$, NC, SH,

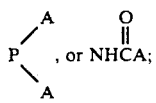

R$^3$ is H, R, SR,

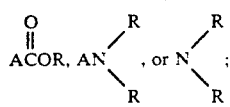

R$^1$ and R$^2$, independently, are A, SA, O—A,

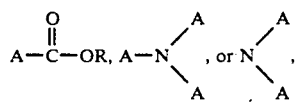

or R$^1$ and R$^2$, when taken together with the carbon atoms to which they are directly attached, can form an aryl group such that Y has the general formula

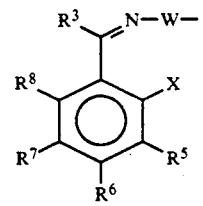

wherein
W, X and R$^3$ are as defined above, and
R$^5$, R$^6$, R$^7$ and R$^8$, independently, are H, OH, R, CO$_2$R,

NO$_2$, F, Cl, Br, I, CF$_3$,

or NA$_3$+I—, or R$^7$ and R$^8$, when taken together with the carbon atoms to which they are directly attached, can form an aryl group having 6 to 10 carbon atoms;

Q is a branched or unbranched, saturated or unsaturated alkyl group having from 1 to 4 carbon atoms;

A is a branched or unbranched, saturated or unsaturated alkyl group having from 1 to 10 carbon atoms and R is a branched or unbranched, unsaturated or saturated alkyl, alkoxy, alkoxyalkyl, acyl alkylacyl, alkoxyacyl, hydroxyalkyl, hydroxyalkylamine, alkylamide, alkylamine, acylamine or acylalkylamine wherein each alkyl or acyl portion has 1 to 10 carbon atoms, or R is an aryl group which can be further substituted with one or more alkoxy or saturated or unsaturated alkyl groups each having 1 to 10 carbon atoms or with an aryl or aryloxy group having 6 to 10 carbon atoms.

The ligands of Formula I are generally prepared from the reaction of a triamine and a salicylaldehyde derivative (SAL). Specific examples of salicylaldehyde derivatives include 5-methyl salicylaldehyde and 4-methoxy salicylaldehyde. The preferred triamine for use in these reactions is tris(aminomethyl)ethane (TAME). The resulting ligands may be referred to as (sal)$_3$tames.

These ligands have the general formula

wherein Z and R⁴ are as defined above and where Z=B, the ligand is ammonia. The three Y groups, which can be the same or different, also are as defined above, that is, each Y group has the general formula

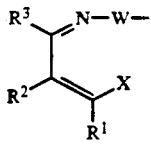

wherein X, W, R¹, R² and R³ are as defined above.

Optionally, it has been found that ligands which correspond to those illustrated above but which have a reduced amine in place of the illustrated imine portion of Y surprisingly can be substituted for the (sal)₃tames in the reaction with technetium to form the same technetium complexes set forth above. Some advantages in stabilization during reaction in acidic media can be realized by the optional use of these amine-containing ligands. These compounds can be referred to simply as "reduced saltames."

The general synthesis of the (sal)₃tames and the reduced analogs thereof of this invention involves the condensation of one equivalent of triamine and three equivalents of a salicylaldehyde derivative. The reaction generally involves the use of anhydrous alcohol, preferably methanol or ethanol. The percentage of reagents required for these reactions is fixed by the stoichiometric requirements of the individual reaction being carried out. Since these reactions are relatively quantitative, depending on the purity of the starting materials and the lack of attention to optimizing purification steps, no work is necessary to optimize the yields of these reactions. Generally, reduction of these compounds using sodium borohydride in methylene chloride is satisfactory for preparation of the reduced (Sal)-₃tames. Representative conditions under which these reactions can be carried out are provided in the examples set forth below. The ligands of the present invention may be produced by using appropriate starting compounds. Thus, to produce the desired ligand, persons skilled in the art will choose an appropriate triamine for reaction with the appropriate salicylaldehyde derivative.

A general synthetic scheme for producing the triamines, aldehydes and resulting tame complexes is shown below:

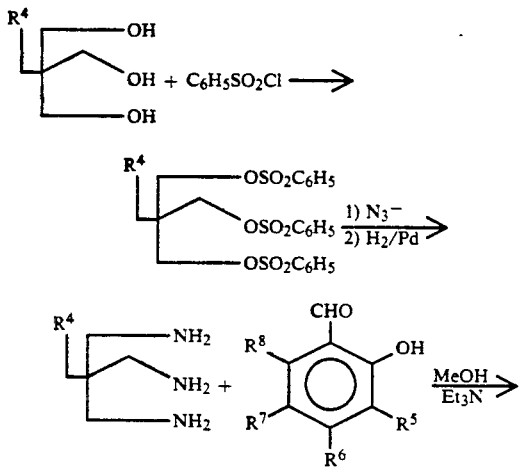

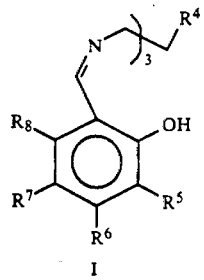

I

The ligands of Formula I, above, may be complexed with a radionuclide metal ion, specifically, a technetium ion. The preferred radionuclide is technetium-99 m. The ligands of the present invention form novel and useful radionuclide metal ion-ligand complexes.

A technetium-99 m ligand complex in accordance with the present invention can be formed by reacting a ligand of Formula I with the technetium-99 m in solution, e.g., saline. Preparation of complexes with technetium-99 m is best accomplished when the radionuclide is in the form of pertechnetate ion, TcO₄—. The pertechnetate ion can be obtained from commercially available technetium-99 m parent-daughter generators when such technetium is in the +7 oxidation state. The generation of the pertechnetate ion using this type of generator is well known to those skilled in the art and is described in more detail in U.S. Pat. Nos. 3,369,121 and 3,920,995. These generators are usually eluted with saline solution and the pertechnetate ion is obtained as the sodium salt. In most cases, to be complexed with a ligand, the oxidation state of the technetium must be reduced to ⇌6 or lower. Deutsch et al. Prog. Inorg. Chem., 30:75-139 (1983). The technetium in the complexes of the present invention can be in a +3 or +4 oxidation state. The chemistry of technetium involves reduction of TcO₄— followed by, or concomitant with substitution.

In one embodiment of the present invention, the ligands described herein are complexed with Tc-99 m by the following process. First, Na⁹⁹ᵐTcO₄ is eluted from a Mo/Tc generator in saline and water is removed in vacuo. Reagent grade absolute alcohol is added and swirled and removed in vacuo. The amount of Na⁹⁹ᵐTcO₄ required for the reaction generally will be between about 0.1 and about 200 mCi. The alcohol step is repeated and the Na⁹⁹ᵐTcO₄ is reconstituted in alcohol. Many different alcohols can be used in this process. An alcohol is selected for a particular reaction based on the solubility of the ligand of interest therein. The preferred alcohol is ethanol, either pure ethanol or any ethanol/water mixture down to 50% ethanol.

A (sal)₃tame ligand then is added to the alcohol-Na⁹⁹ᵐTcO₄ solution and is dissolved by sonication. The ligand used may be any of those disclosed in the present application and may be in an amount from about 1 to about 25 mg per 1 to about 5 ml of alcohol-Na⁹⁹ᵐTcO₄ solution, depending on the solubility of the particular ligand in the alcohol.

The reaction mixture generally also will contain a pertechnetate reducing agent. The reducing agent must be capable of reducing heptavalent technetium (TcO₄—) to trivalent, tetravalent and/or pentavalent technetium. Suitable pertechnetate reducing agents include metallic salts of sulfuric acid and hydrochloric acid, such as stannous chloride, chromous chloride and ferrous sulfate. Other agents capable of reducing pertechnetate-99 m include, for example, titanous halides, thiosulfate, hydrazine, iron colloids, dithionite or formamidine sulfinic acid and acidborohydrides. U.S. Pat. Nos. 3,735,001 granted May 22, 1973; 3,863,004 granted Jan. 28, 1975; 3,466,361 granted Sept. 9, 1969; 3,720,761 granted Mar. 13, 1973; 3,723,612 granted Mar. 27, 1973; 3,725,295 granted Apr. 3, 1973; 3,803,299 granted Apr. 9, 1974; and 3,749,556 granted July 31, 1973 (all incorporated herein by reference) disclose various pertechnate reducing agents comprising reducing ions capable of reducing heptavalent pertechnetate to appropriate lower valence states. Free metals such as tin also are known for use as pertechnetate reducing agents, although undissolved metal must be removed from the scanning solution prior to injection into the patient. Thus, it is more convenient to use metal compounds which provide a reducing metal cation in injectable, water-soluble form.

Water-soluble stannous ($Sn^{+2}$) compounds, especially stannous chloride, are preferred for use as the pertechnetate reducing agent herein. Stannous bromide, fluoride and sulfate also can be used. Stannous salts of organic acids, such as stannous tartrate or maleate, can be used, as can the stannous salt of methanehydroxydiphosphonic acid.

Although not wishing to be bound by any theory, it is believed that the (sal)$_3$tame ligands form a complex with technetium wherein the technetium is in a +4 oxidation state. This gives the whole molecule a +1 charge. In addition, it is believed that in some cases the variation of substituents on the ligand can allow the technetium to exist in a +3 oxidation state in vitro, thus giving the complex an overall neutral charge.

The reaction mixture is heated for between about 0.5 to about 2 hours and, after cooling, is diluted with water and filtered. The dilution ratios with water may be between about 1:2 to about 1:500 of reaction solution to water. The preferred filter for use in the filtration step is a 0.2 $\mu$m filter. The resulting clear solution is purified by HPLC and diluted to the concentration necessary for animal studies using normal saline. Normally, 0.9% saline is used. There is no limit on dilution, but for clinical studies, a ratio of about 1:10 is preferred to lower the ethanol concentration from the HPLC to less than 10%.

The radiopharmaceutical compositions may optionally, but preferably, contain a sufficient amount of a stabilizer material to prevent or inhibit the oxidation of the pertechnetate reducing agent (e.g., oxidation of $Sn^{+2}$ to $Sn^{+4}$) during storage and/or to inhibit or reduce the reoxidation of reduced technetium-99 m and/or to reduce the formation of technetium-labeled impurities which can result from the synthetic method or form during use of the compositions.

The stabilizers which may be used with the ligand-radionuclide complexes of the present invention are characterized by their toxicological acceptability under the conditions of use, their ability to stabilize the product for a reasonable period of storage and/or under usage conditions, and by their substantial non-interference with the delivery of the technetium radionuclide to bone mineral.

Stabilizers which meet the foregoing requirements and which are quite suitable for intravenous injection include gentisic acid and its water-soluble salt and esters, reductic acid and its water-soluble salts and esters, ascorbic acid and its water-soluble salts and esters, and p-aminobenzoic acid and its water-soluble salts and esters. Gentisic acid, reductic acid, ascorbic acid and p-aminobenzoic acid are all known, commercially available materials. The sodium salts of these acids are all available, quite water-soluble, and preferred for use herein. Other suitable stabilizers include lyophilization stabilizers, such as mannitol, lactose and dextrose, and antimicrobial agents.

As is known in the literature, stabilizer materials such as ascorbic acid can chelate/complex with technetium and cause it to be deposited in soft tissue. Since the practitioner of the present invention will wish to avoid all unnecessary deposition in soft tissue, it will be appreciated that the amount of stabilizer material optionally used in the present compositions should not be so great as to compete with the ligand of choice, thereby interfering with the scan.

The compositions of the present invention are for intravenous injection into humans or lower animals. Accordingly, appropriate manufacturing and operating conditions are employed to provide sterile, pyrogen-free compositions.

The compositions of the present invention can be prepared by combining the ligand, the reducing agent, if needed, and optional stabilizer. The mixture may be dry blended or in a solution, e.g., alcohol, saline, etc. Various other additives can be incorporated, provided they are non-interfering in the complexation of the technetium or stability of the product. These compositions may be in a freeze-dried form or simply packaged in nitrogen filled containers as an added protection against oxidation of the reducing agent if present. The composition also can be provided in an aqueous solution in sterile, pyrogen-free water. Preferably, the water is deoxygenated and the composition stored under nitrogen, thereby minimizing undesirable oxidation of the reducing agent on storage. Since the reducing agent is more prone to oxidize in solution than in the dry powder and freeze-dried forms, it is preferred that aqueous solutions contain a stabilizer.

Compositions of the foregoing type are characterized by a physiologically-acceptable in-use solution pH in the range from about 3.5 to about 8, and, in the main, fall within a preferred pH range of 4 to about 6.

In one embodiment of the present invention, the compositions of ligand, reducing agent and optional stabilizer can be dissolved with a pertechnetate-99 m isotonic solution from a commercial technetium source to yield an imaging agent suitable for intravenous injection. The ligand generally is used with the reducing agent in a ratio between about 20:1 to about 50:1. Generally, Tc-99 m of greater than 100 mCi/ml in ethanol is used. The stability of such scanning agents is ample under ordinary hospital conditions. Administration is preferably done within about eight hours after addition of the pertechnetate solution.

The concentration of reagents, including the Tc-99 m, will depend on the type of mammal receiving the composition. The total dosage of radionuclide for a sharp skeletal or myocardial infarct scan in humans, for example, ranges from about 5 millicuries to about 30 mCi/ml, preferably from about 5 mCi to about 20 mCi/ml. In humans, it generally is sufficient that about 1-5 ml of the solution is used in an adult of about 50-100 kg body weight. The concentration best suited for rats is between about 10 and 50 $\mu$Ci/ml. The concentration recommended for guinea pigs is between about 30 and 70 $\mu$Ci/ml. For dogs, for imaging purposes, the concentration is preferably between about 0.75 and about 1.25 mCi/ml. Since the technetium complexes of the present invention provide such sharp scan quality and minimize soft tissue uptake, the total exposure of the patient to radionuclide can be minimized.

The following examples are illustrative only and are not meant to limit the scope of the invention as set forth in the appended claims.

EXAMPLE 1

The synthesis of a triamine for use in the synthesis of the ligands of the present invention is shown below.

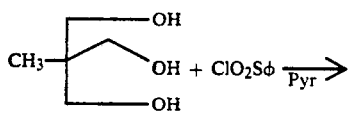

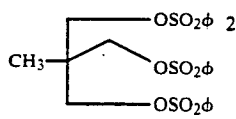

Tris (hydroxymethyl)ethane (126 g, 1.05 mol) was dissolved in 550 ml (6.8 mol) of pyridine and stirred at 0° C. Benzenesulfonyl chloride (480 ml, 3.76 mol) was added dropwise. After the addition was complete (3½ h) the pink suspension was stirred at room temperature for 16 hrs. The mixture was then poured into a solution of 2000 ml MeOH, 1000 ml H₂O and 800 ml concentrated HCl. The pink solid that formed was crushed into small pieces in a mortar and the solid was collected, washed with 3000 ml H₂O and 500 ml of CH₃OH and dried. The solid material was recrystallized from acetone (650 ml) to give 354 g of white needles. The melting point was 104°–106° C. The literature melting point is 105°–106° C. There was a 62% yield. The mother liquor was evaporated to give 101 g (18%) of white solid with a melting point of 103°–106° C., giving an 80% total yield.

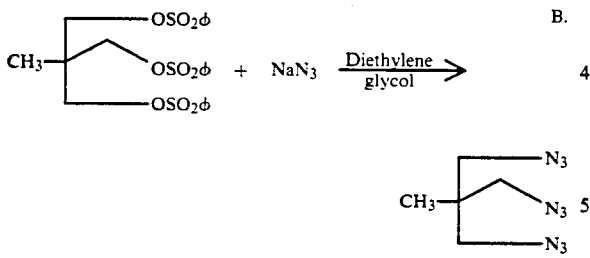

The tribenzenesulfonyl ester (350 g, 648 mmol), and sodium azide (210 g, 3.2 mol) were stirred together in 1000 ml of diethylene glycol at 135° C. for 16 hrs. The mixture was poured into 2500 ml of H₂O. Only a slight amount of oil separated so the aqueous mixture was extracted with EtOAc in 500 ml batches. 3000 ml of EtOAc were used altogether. The EtOAc extracts were combined, washed with H₂O and brine and added to a flask containing MgSO₄ and activated charcoal. After stirring for 30 minutes, the solution was filtered and evaporated to leave 110 g (87%) of light yellow oil. Since the resulting material was IR consistent, this material was used in the next step without further purification. The compound was ¹H and ¹³C NMR consistent.

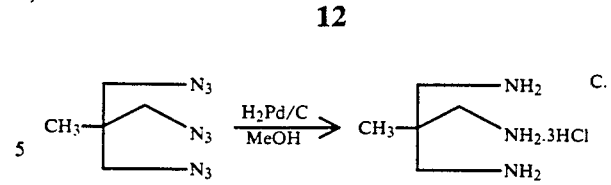

The triazide (110 g, 564 mmol) was diluted with 1500 ml of absolute methanol. 10% Pd/C (10 g) was added to this solution in a 2000 ml Parr bottle under argon. This material was hydrogenated at 30 psi for 72 hrs. The reaction was monitored by TLC and IR for disappearance of the starting material. Even though a slight amount of starting material remained by IR, the hydrogenation was stopped and the catalyst was removed by filtration. The solution was cooled in an ice bath and concentrated HCl was added until the apparent pH was 2. The white precipitate was removed by filtration, washed with MeOH and ether and dried overnight under vacuum to give 67 g (53%) of white powder. The compound was ¹H and ¹³C NMR consistent. This material was used without further purification in the procedures shown in Examples 3 and 4 to produce ligands useful in forming the complexes of the present invention.

EXAMPLE 2

An alternative method of synthesizing a triamine for production of the ligands described herein is shown below.

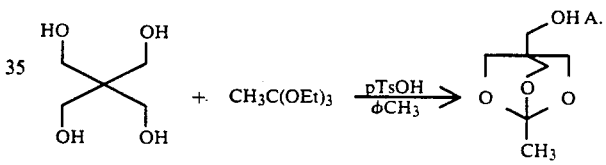

Pentaerythritol (136 g, 1.0 mol), triethyl orthoacetate (162 g, 1.0 mol) and p-toluenesulfonic acid (750 mg) were heated together in 100 ml of toluene at 100° C. The ethanol that formed was distilled off (140 ml). The temperature was raised and 80 ml of toluene was removed by distillation. The residue was dried under reduced pressure to leave an oil. This oil was distilled in a kugelrohr, or short path distillation column. After a portion of oil distilled over, the flask was changed and 128 g of white solid sublimed into the receiving flask. The compound was ¹H and ¹³C NMR consistent.

Powdered potassium hydroxide (24.0 g, 429 mmol) was stirred in dimethyl sulfoxide (150 ml) at room temperature. The alcohol (15.0 g, 93.8 mmol) was added followed by the slow addition of propyl iodide (25 ml, 256 mmol). The solution became very hot and bubbled vigorously. After 40 minutes it was poured into 1500 ml of water. The product was extracted into ether, washed with water and brine, dried over MgSO₄, filtered and evaporated to leave 12.8 g (68%) of clear oil. The compound was $^1$H and $^{13}$C NMR consistent.

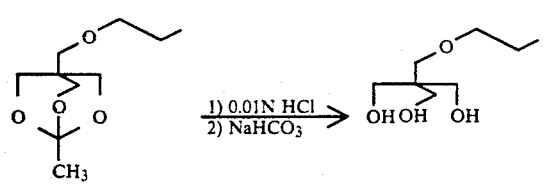

C.

The product of the previous reaction (12.8 g, 63.4 mmol) was stirred in 260 ml of 0.01 N HCl and 80 ml of methanol for 2 hours at room temperature. Solid NaHCO$_3$ (5.6 g) was added and the solution was stirred for an additional hour. The solvent was removed under reduced pressure. Methanol was added to the dry residue and the inorganic material was removed by filtration. The filtrate was evaporated to leave 11.5 g (100%) of the trialcohol as a clear oil. The compound was $^1$H and $^{13}$C NMR consistent.

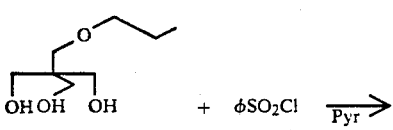

D.

The trialcohol (11.5 g, 64.6 mmol) was dissolved in 35 ml of pyridine. This solution was stirred at room temperature. Benezenesulfonyl chloride (27.8 ml, 218 mmol) was added dropwise. This solution was stirred for 24 hours, then was poured into 60 ml of concentrated HCl in 200 ml of water. The crude product was extracted into Et$_2$O/CHCl$_3$, washed with 5% NaHCO$_3$ and brine, dried over MgSO$_4$, filtered and evaporated. The crude solid was washed with hexanes, filtered and dried to give 33.7 g (87%) of the tribenzenesulfonate as a white solid. The compound was $^1$H and $^{13}$C NMR consistent.

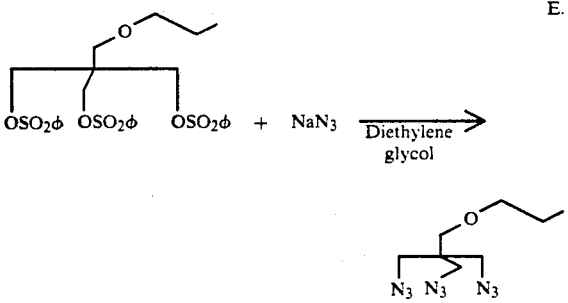

E.

The tribenzenesulfonate (33.5 g, 56.0 mmol) was heated at 135° C. with sodium azide (18.2 g, 280 mmol) in 100 ml of diethylene glycol for 18 hours. The mixture was poured into 200 ml of water. The crude azide was extracted into ether. This solution was washed with water and brine, dried over MgSO$_4$, decolorized with charcoal, filtered and evaporated to give 13.5 g (95%) of the triazide as a clear oil. The compound was $^1$H and $^{13}$C NMR consistent.

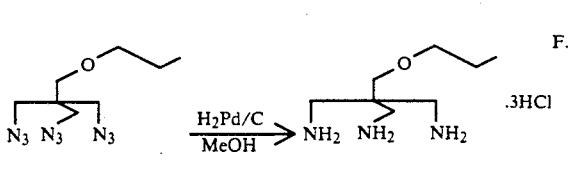

F.

The triazide (13.5 g, 53.4 mmol) was stirred in 300 ml of anhydrous methanol at room temperature. Pd/C (2 g of 10%) was added in 5 ml of water and H$_2$ was bubbled over the top of this mixture for 72 hours. After purging the flask with nitrogen, the catalyst was removed by filtration. HCl(g) was bubbled through this solution for 10 min. The solvent was evaporated and the solid material was washed with ether, filtered and dried to give 13.5 g (89%) of white solid. This material was used without further purification in the procedures shown in Examples 8 and 9 to produce ligands useful in forming complexes of the present invention.

EXAMPLE 3

The synthesis of an unsymmetrical triamine for use in the synthesis of ligands of the present invention is shown below.

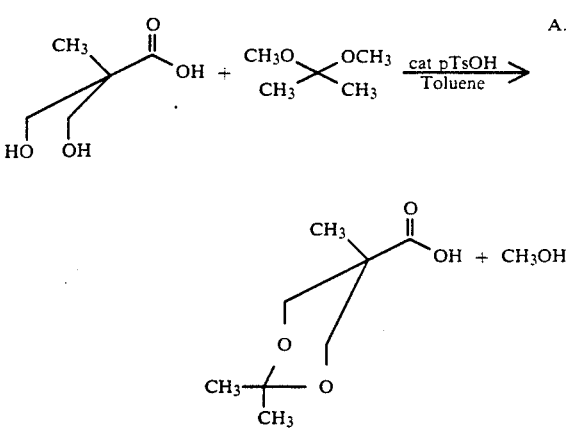

A.

A mixture of 2,2-bis(hydroxymethyl)propionic acid (26.6 g, 199 mmol), 2,2-dimethoxypropane (20.7 g, 198.7 mmol) and p-toluenesulfonic acid (50 mg) were heated to reflux together in toluene (200 ml). The methanol which was formed was distilled from the pot. After the theoretical amount of methanol was distilled (2 hrs.) another portion of 2,2-dimethoxypropane (12 g, 115 mmol) was added and the mixture was allowed to cool and stir for 12 hrs. Concentration afforded a dark solid. The material was taken up into ether (160 mol) and precipitated with the copious addition of hexanes. Filtration afforded pure acetonide, 18 g (52%) as a white powder. The compound was $^1$H and $^{13}$C NMR consistent.

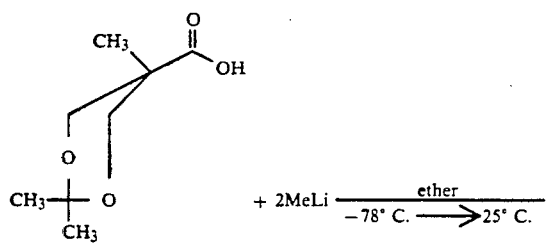

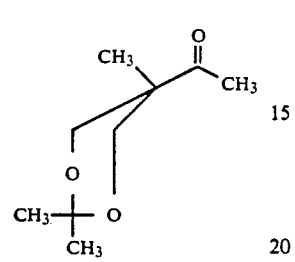

To the acid (5.0 g, 28.7 mmol) in anhydrous ether (20 ml) at −78° C. was added methyllithium (50 ml of a 1.2 M solution in ether, 60 mmol) dropwise. The mixture was stirred for 1 hour post-addition and allowed to warm to room temperature and stir an additional 2 hours. The mixture was cooled to −20° C. and poured into a 95% aqueous methanol solution kept at −25° C. After dilution with water (100 ml) the layers were separated and the aqueous portion was extracted with ether (2×250 ml). The combined etheral extracts were dried (K$_2$CO$_3$) and concentrated to afford pure methyl ketone, 4.15 g (84%). The compound was $^1$H and $^{13}$C NMR consistent.

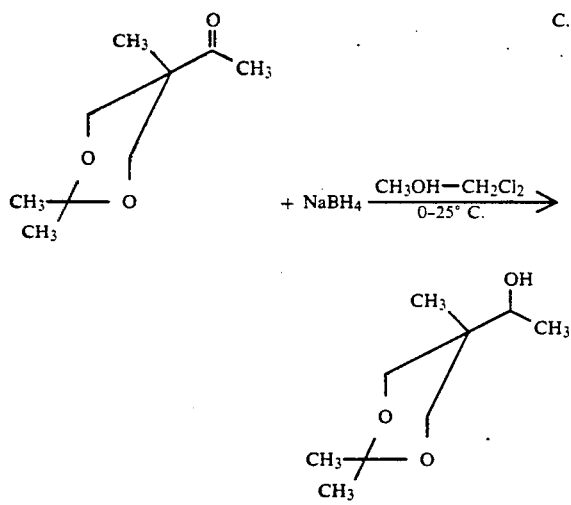

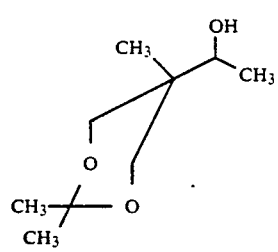

To the methyl ketone (4.15 g, 24.2 mmol) in CH$_3$OH—CH$_2$Cl$_2$ (20 ml of a 1:1 solution) was added NaBH$_4$ (1 g, 26.4 mmol) at 0° C. The mixture was allowed to warm to room temperature and stir for 1.5 hrs post-addition. After this time the reaction mixture was poured onto ice (50 g) and diluted with water (100 ml). The layers were separated and the aqueous portion was extracted with CH$_2$Cl$_2$ (3×75 ml). The combined CH$_2$Cl$_2$ extract was dried (Na$_2$SO$_4$), and concentrated to provide the secondary alcohol, 3.66 g (86.8%). The compound was 1H and $^{13}$C NMR consistent and was used in the next step without further precipitation.

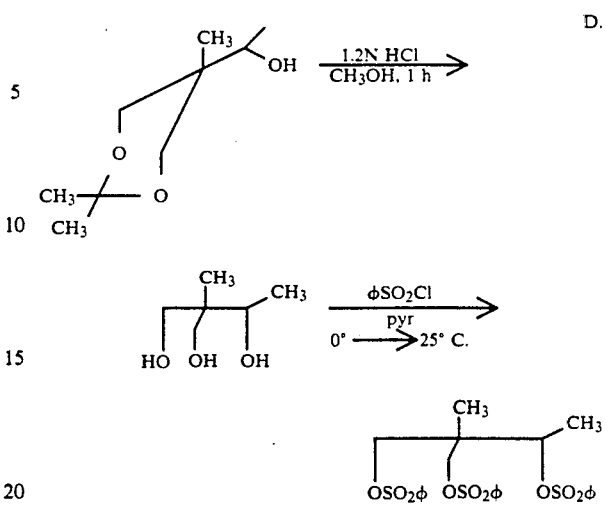

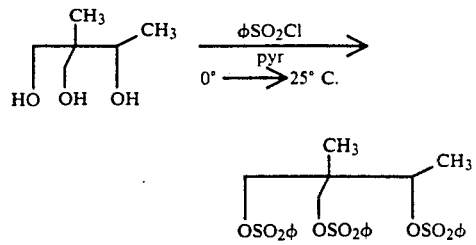

To the secondary alcohol (3.66 g, 21 mmol) in CH$_3$OH (20 ml) was added 1.2 N HCl (18 ml) and the resulting warm solution was stired for 1 hr at room temperature. The CH$_3$OH was evaporated and the aqueous solution was washed with ether (25 ml) and evaporated to give a thick colorless oil, 1.61 g (57%). The triol (1.61 g, 12 mmol) was dissolved in pyridine (30 ml) and treated with benzenesulfonyl chloride (5.5 ml, 43 mmol) dropwise at 0° C. After addition was complete the pink suspension was stirred at room temperature for 12 hrs. The suspension was then poured into a mixture of water (45 ml) and concentrated HCl (15 ml). The resulting suspension was extracted with CH$_2$Cl$_2$ (3×50 ml) and the combined extracts were dried (Na$_2$SO$_4$). Concentration afforded the pure tribenzenesulfonate as a white solid, 5.4 g (81%). The compound was $^1$H and $^{13}$C NMR consistent.

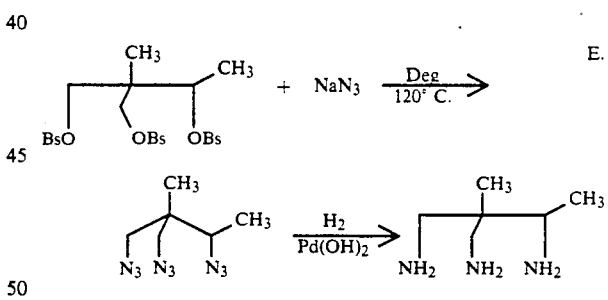

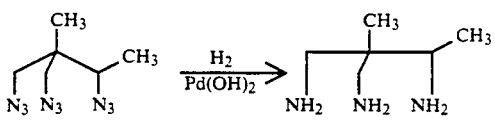

To the tribenzenesulfonate (5.76 g, 10.4 mmol) in Diethylene glycol (30 ml) was added NaN$_3$ (3 g, 48 mmol) and the mixture was heated to 120° C. for 12 hours. The mixture was allowed to cool and poured into water (65 ml). The resulting suspension was extracted with ether (3×50 ml) and combined ethereal extracts were dried (Na$_2$SO$_4$) and concentrated. This compound was $^1$H and $^{13}$C NMR consistent and was used in the next step without further purification. The resulting mobile oil was dissolved in CH$_3$OH (50 ml), treated with Pd(OH)$_2$ (530 mg) and subjected to a continuous flow of H$_2$ (1 atm) for 10 hr. The catalyst was filtered and the solution was concentrated to afford the triamine, 1.02 g (75%). This product was IR consistent and was used in the procedures of Example 10 to synthesize a ligand useful in forming complexes of the present invention.

EXAMPLE 4

A salicylaldehyde compound for use in the production of the ligands of the present invention was synthesized by the following procedure.

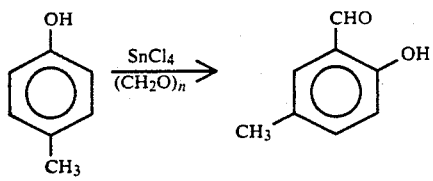

A.

4-Methylphenol (27 g, 250 mmol), tin (IV) tetrachloride (2.9 ml, 25 mmol) and tri-n-butylamine (23.7 ml, 100 mmol) were stirred together in 50 ml of toluene at room temperature under argon for 20 min. Paraformaldehyde (16.5 g) was added and the solution was heated at 100° C. for 7 hours. The reaction mixture was poured into 1000 ml of water and made acidic with 3N HCl. The resulting suspension was extracted several times with Et$_2$O. The Et$_2$O washes were combined, dried and evaporated. The residue was chromatographed on a large column of silica gel (Hexanes→Hexanes/Et$_2$O 9/1) The first UV active component was collected and evaporated to leave 5.4 g of white solid (16% yield). The compound was $^1$H and $^{13}$C NMR consistent.

The triamine of Example 1 was reacted with the salicylaldehyde prepared by the procedure directly above to produce the desired (sal)$_3$tame compound:

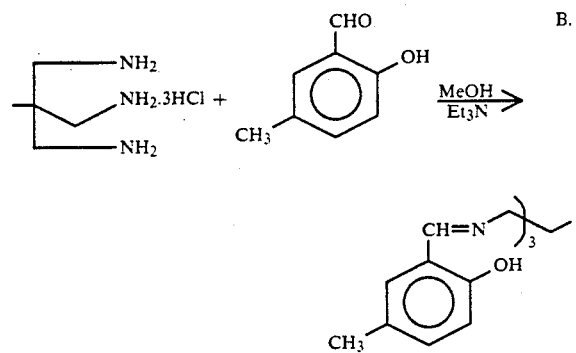

B.

500 mg (2.2 mmol) of the triamine trihydrochloride was suspended in 25 ml of anhydrous methanol. Triethylamine (0.92 ml, 6.6 mmol) was added and this mixture was stirred at room temperature until clear. 901 mg (6.6 mmol) of the aldehyde was added and the solution was heated to boiling on the steam bath. The solution was allowed to cool slowly, then placed in the freezer overnight. The crystals that separated were removed by filtration (940 mg) and recrystallized from methanol to give 870 mg of yellow needles with a melting point of 140°-144° C. (84% yield). The compound was IR and $^1$H and $^{13}$C NMR consistent.

TLC (Silica, Hex/EtoAc 8/2) Rf=0.60.

Analysis Calculated for C$_{29}$H$_{33}$N$_3$O$_3$: C, 73.89; H, 7.01; N,8.92.

Found: C, 73.89; H, 7.16; N, 8.84.

EXAMPLE 5

5-(Methylsal)$_3$tame, synthesized in the preceding example, was converted to the corresponding reduced (sal)$_3$tame by the following procedure:

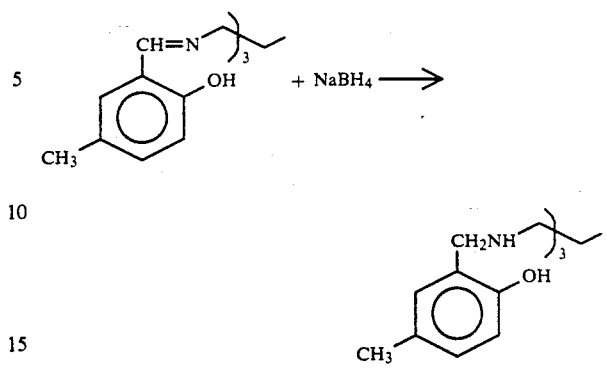

5-Methylsal$_3$tame (704 mg, 1.5 mmol) was dissolved in 10 ml of methylene chloride. Methanol (10 ml) was added and this solution was stirred in an ice bath. Sodium borohydride (170 mg, 4.5 mmol) was added. The ice bath was removed and the solution was stirred at room temperature for one hour. The solution was poured into ethyl acetate, washed with water and brine, dried over MgSO$_4$, filtered and evaporated to give 620 mg (87%) of white solid. This solid was chromatographed on a short plug of silica gel (Et$_2$O→20% EtOAc/H$_2$O) to give 410 mg of solid. Recrystallization from EtOAc/Hexanes provided 380 mg of white crystals. The melting point was 104°-106° C. The compound was IR and $^1$H and $^{13}$C NMR consistent.

TLC (Slica, Et$_2$O) Rf=0.24;

EI mass spectrum m/e=477 (M).

Analysis calculated for C$_{29}$H$_{39}$N$_3$O$_3$: C, 72.96; H, 8.18; N, 8.81.

Found: C, 73.00; H, 8.26; N, 8.79.

EXAMPLE 6

The triamine of Example 1 was reacted with a salicylaldehyde to produce a (sal)$_3$tame as shown:

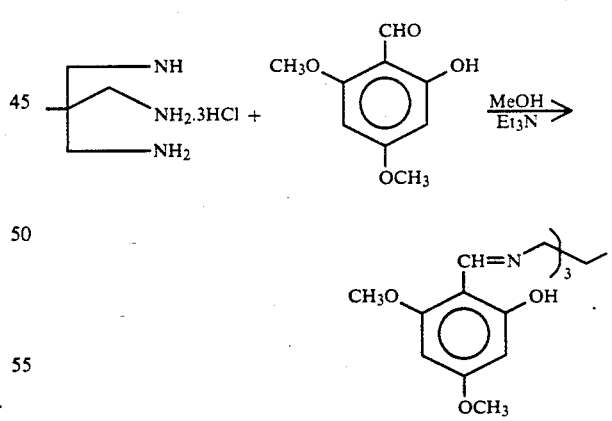

500 mg (2.2 mmol) of the triamine.trihydrochloride was suspended in 25 ml of anhydrous methanol. Triethylamine (0.92 ml, 6.6 mmol) was added and this mixture was stirred at room temperature until clear. 1.2 g (6.6 mmol) of the aldehyde was added and the solution was heated on the steam bath and then cooled overnight. No crystals developed so the solvent was evaporated. After removal of a few ml of MeOH, crystals separated. The solution then was cooled and 1.2 g of solid were isolated by filtration. These crystals were recrystallized from methanol to give 1.05 g (78%) of dark yellow crystals with a melting point 78°-82° C.; TLC (Silica, EtOAc) Rf=0.40. This compound was IR and proton and $^{13}$CNMR consistent.

EXAMPLE 7

The triamine of Example 1 was reacted with acetyl acetone, as described below, to synthesize the ligand shown.

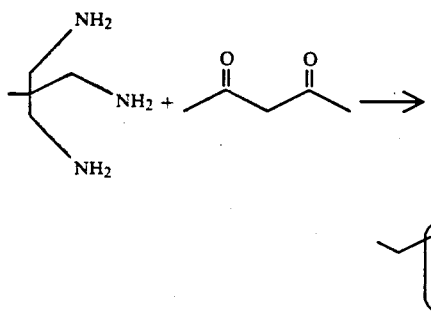

A solution of the triamine (750 mg, 6.4 mmol) and acetylacetone (10 ml) in 40 ml. of benzene was refluxed for one hour. The solvents were removed by evaporation. The solid residue was recrystallized from EtOAc/hexanes, yielding 650 mg (30%) of light yellow needles. The melting point was 88°-90° C. The compound was IR and proton and $^{13}$C NMR consistent.

TLC (silica; EtOAc) Rf=0.25.
Analysis calculated for $C_{20}H_{33}N_3O_3$:
C, 66.12; H, 9.09; N, 11.57.
found: C, 66.37; H, 9.28; N, 11.36.

EXAMPLE 8

The triamine of Example 2 was reacted with a salicylaldehyde to produce a substituted (sal)$_3$tame as shown.

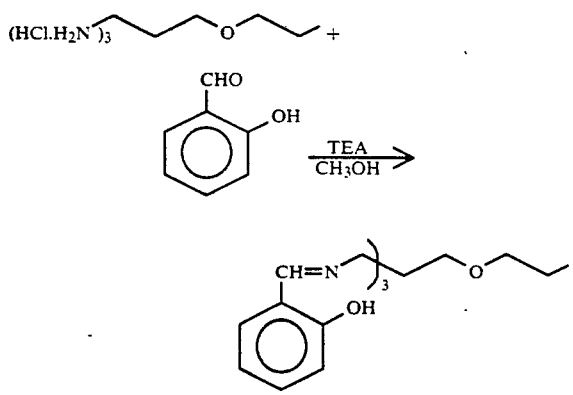

The triamine trihydrochloride (2.0 g, 7.0 mmol) was dissolved in 40 ml of methanol containing 2.93 ml (21 mmol) of triethylamine. Salicylaldehyde (2.57 g, 21 mmol) was added and the yellow solution was heated to reflux for a few minutes. The solvent was evaporated and the residue was taken up into ether, washed with water and brine, dried over MgSO$_4$, filtered and evaporated. The residue was chromatographed (Silica 10% Et$_2$O/Hexanes→ 1/1 Et$_2$O/Hexanes) to give 1.88 g (55%) of yellow oil. Seed crystals were added and the oil solidified slowly. The solid was slurried in cold hexanes and filtered to give 1.38 g (40%) of yellow powder. The compound was $^1$H and $^{13}$C NMR consistent.

TLC (Silica; Hexanes/Et$_2$O 4/1) Rf=0.30.
CI Mass spectrum m/e - 488 (M+1).
Analysis Calculated for $C_{29}H_{33}N_3O_4$: C, 71.46; H, 6.78; N, 8.62.
Found: C, 71.54; H, 6.84; N, 8.60.

EXAMPLE 9

The triamine of Example 2 was used to synthesize a (sal)$_3$tame as shown below.

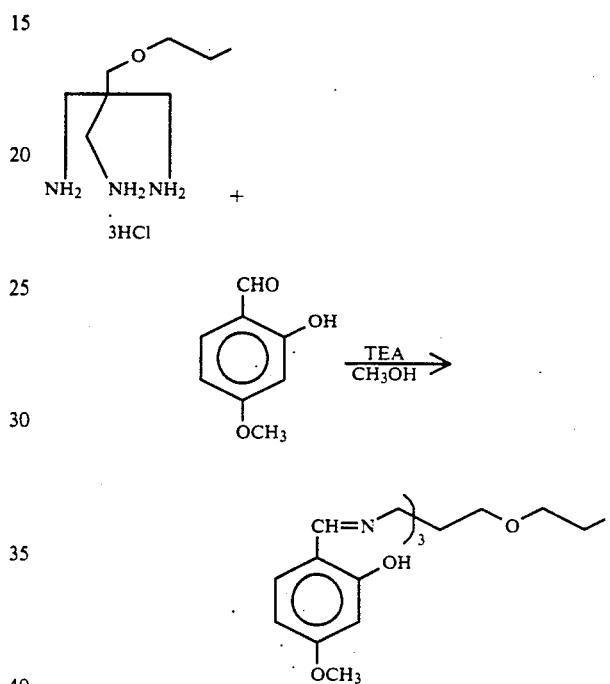

The triamine trihydrochloride (500 mg, 1.8 mmol) was dissolved in 10 ml of methanol containing 0.75 ml (5.3 mmol) of triethylamine. 4-methoxysalicylaldehyde (801 mg, 5.3 mmol) was added and the solution was heated to reflux for a few minutes. The solvent was evaporated and the residue was taken up into ether, washed with water and brine, dried over MgSO$_4$, filtered and evaporated. The residue was chromatographed (Silica 1/1 Et$_2$O/Hex→ Et$_2$O) to give 530 mg (52%) of yellow oil. The compound was $^1$H and $^{13}$C NMR consistent.

TLC (Silica, Et$_2$O) RF=0.70.
EI mass spectrum m/e=577.

EXAMPLE 10

The unsymmetrical triamine of Example 3 was reacted with the salicylaldehyde shown below to produce the desired (sal)$_3$tame compound:

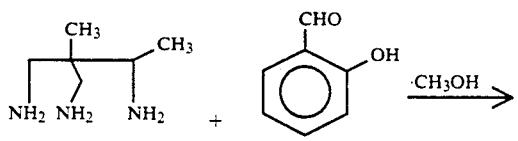

-continued

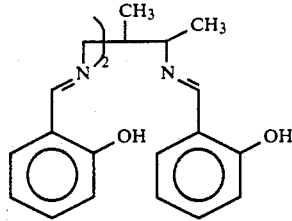

To a solution of the triamine (1.02 g, 7.7 mmol) in CH$_3$OH (20 ml) was added salicylaldehyde (2.5 ml, 23 mmol) and the reaction was heated to reflux for 5 min on a steam bath and concentrated to afford an orange-brown oil. The product was purified by flash column chromatography on SiO$_2$ using (4:1) hexanes-EtOAc affording 1.21 g (35%). The compound was IR, $^1$H and $^{13}$C NMR consistent.

TLC (Silica, 4:1 hexanes-EtOAc) Rf=0.25.

EI Mass Spectrum m/e=443.

EXAMPLE 11-94

The compounds listed in Table I were synthesized using the procedures substantially in accordance with those of Examples 1-10.

TABLE I

| R¹ | R² | R³ | R⁴ | R⁵ | R⁶ | R⁷ | R⁸ | X | W | Z |
|---|---|---|---|---|---|---|---|---|---|---|
| methyl-4-hydroxybenzoate, 3,3'-[[[(5-carbomethoxy-2-hydroxyphenyl)methylene]amino]-2-methyl-1,3-propanediyl]bis(nitrilomethylidyne)]bis- | | | | | | | | | | |
| 6 carbon | 6 carbon | H | $CH_3$ | H | H | $-CO_2CH_3$ | H | OH | $CH_2$ | C |
| aryl with R² | aryl with R¹ | | | | | | | | | |
| phenol, 2,2'-[[[(2-hydroxyphenyl)ethylene]amino]methyl]-2-methyl-1,3-propanediyl]bis(nitrilomethylidyne)]bis- | | | | | | | | | | |
| 6 carbon | 6 carbon | $CH_3$ | $CH_3$ | H | H | H | H | OH | $CH_2$ | C |
| aryl with R² | aryl with R¹ | | | | | | | | | |
| 4-methoxyphenol, 2,2'-[[[(5-methoxy-2-hydroxyphenyl)methylene]amino]methyl]-2-methyl-1,3-propanediyl]bis(nitrilomethylidyne)]bis- | | | | | | | | | | |
| 6 carbon | 6 carbon | H | $CH_3$ | H | H | $OCH_3$ | H | OH | $CH_2$ | C |
| aryl with R² | aryl with R¹ | | | | | | | | | |
| t-octylphenol, 2,2'-[[[(5-t-octyl-2-hydroxyphenyl)methylene]amino]methyl]-2-methyl-1,3-propanediyl]bis(nitrilomethylidyne)]bis | | | | | | | | | | |
| 6 carbon | 6 carbon | H | $CH_3$ | H | H | $C(CH_3)_2CH_2C(CH_3)_3$ | H | OH | $CH_2$ | C |
| aryl with R² | aryl with R¹ | | | | | | | | | |
| phenol, 2,2'-[[[(2-hydroxyphenyl)methylene]amino]methyl]-2-methyl-1,3-propanediyl]bis(nitrilomethylidyne)]bis- | | | | | | | | | | |
| 6 carbon | 6 carbon | H | $CH_3$ | H | H | H | H | OH | $CH_2$ | C |
| aryl with R² | aryl with R¹ | | | | | | | | | |
| octylphenol, 2,2'-[[[(5-octyl-2-hydroxyphenyl)methylene]amino]methyl]-2-methyl-1,3-propanediyl]bis(nitrilomethylidyne)]bis- | | | | | | | | | | |
| 6 carbon | 6 carbon | H | $CH_3$ | H | H | octyl | H | OH | $CH_2$ | C |
| aryl with R² | aryl with R¹ | | | | | | | | | |
| 3,5-dimethyl-4-methoxyphenol, 2,2'-[[[(4,6-dimethyl-5-methoxy-2-hydroxyphenyl)methylene]amino]methyl]-2-methyl-1,3-propanediyl]bis(nitrilomethylidyne)]bis- | | | | | | | | | | |
| 6 carbon | 6 carbon | H | $CH_3$ | H | $CH_3$ | $OCH_3$ | $CH_3$ | OH | $CH_2$ | C |
| aryl with R² | aryl with R¹ | | | | | | | | | |
| 2-ethoxyphenol, 6,6'-[[2-[[[(3-ethoxy-2-hydroxyphenyl)methylene]amino]methyl]-2-methyl-1,3-propanediyl]bis(nitrilomethylidyne)]bis- | | | | | | | | | | |
| 6 carbon | 6 carbon | H | $CH_3$ | $O-CH_2CH_3$ | H | H | H | OH | $CH_2$ | C |
| aryl with R² | aryl with R¹ | | | | | | | | | |
| 4-nitrophenol, 2,2'-[[[(5-nitro-2-hydroxyphenyl)methylene]amino]methyl]-2-methyl-1,3-propanediyl]bis(nitrilomethylidyne)]bis- | | | | | | | | | | |
| 6 carbon | 6 carbon | H | $CH_3$ | H | H | $NO_2$ | H | OH | $CH_2$ | C |
| aryl with R² | aryl with R¹ | | | | | | | | | |
| phenol, 2,2'-[[[(2-hydroxyphenyl)methylene]amino]methyl]-1,3-propanediyl]bis(nitrilomethylidyne)]bis- | | | | | | | | | | |
| 6 carbon | 6 carbon | H | $CH_2-\phi$ | H | H | H | H | OH | $CH_2$ | C |
| aryl with R² | aryl with R¹ | | | | | | | | | |
| 2,3,4,5-tetramethoxyphenol, 6,6'-[[2-[[[(3,4,5,6-tetramethoxy-2-hydroxyphenyl)methylene]amino]methyl]-2-methyl-1,3-propanediyl]bis(nitrilomethylidyne)]bis- | | | | | | | | | | |
| 6 carbon | 6 carbon | H | $CH_3$ | $OCH_3$ | $OCH_3$ | $OCH_3$ | $OCH_3$ | OH | $CH_2$ | C |
| aryl with R² | aryl with R¹ | | | | | | | | | |
| phenol, 2,2'-[[[(2-hydroxyphenyl)methylene]amino]methyl]-2-hexyloxymethyl-1,3-propanediyl]bis(nitrilomethylidyne)]bis- | | | | | | | | | | |
| 6 carbon | 6 carbon | H | $CH_2-O(CH_2)_5CH_3$ | H | H | H | H | OH | $CH_2$ | C |
| aryl with R² | aryl with R¹ | | | | | | | | | |
| phenol, 2,2'-[[[(2-hydroxyphenyl)methylene]amino]methyl]-2-propoxymethyl-1,3-propanediyl]bis(nitrilomethylidyne)]bis- | | | | | | | | | | |
| 6 carbon | 6 carbon | H | $CH_2-O(CH_2)_2CH_3$ | H | H | H | H | OH | $CH_2$ | C |
| aryl with R² | aryl with R¹ | | | | | | | | | |
| 3,5-dimethoxyphenol, 2,2'-[[[(4,6-dimethoxy-2-hydroxyphenyl)methylene]amino]methyl]-2-propoxymethyl-1,3-propanediyl]bis(nitrilomethylidyne)]bis- | | | | | | | | | | |
| 6 carbon | 6 carbon | H | $CH_2-O(CH_2)_2CH_3$ | H | $OCH_3$ | H | $OCH_3$ | OH | $CH_2$ | C |
| aryl with R² | aryl with R¹ | | | | | | | | | |
| phenol, 2,2'-[[[(2-hydroxyphenyl)methylene]amino]methyl]-2-ethoxymethyl-1,3-propanediyl]bis(nitrilomethylidyne)]bis- | | | | | | | | | | |
| 6 carbon | 6 carbon | H | $CH_2-O-CH_2CH_3$ | H | H | H | H | OH | $CH_2$ | C |
| aryl with R² | aryl with R¹ | | | | | | | | | |
| 2-methoxyphenol, 6,6'-[[2-[[[(3-methoxy-2-hydroxyphenyl)methylene]amino]methyl]-2-propoxymethyl-1,3-propanediyl]bis(nitrilomethylidyne)]bis- | | | | | | | | | | |
| 6 carbon | 6 carbon | H | $CH_2-O(CH_2)_2CH_3$ | $OCH_3$ | H | H | H | OH | $CH_2$ | C |
| aryl with R² | aryl with R¹ | | | | | | | | | |
| 1',1',1'-tris(5-fluoro-2-hydroxyacetophenoniminemethyl)ethane | | | | | | | | | | |

TABLE I-continued

| R¹ | R² | R³ | R⁴ | R⁵ | R⁶ | R⁷ | R⁸ | X | W | Z |
|---|---|---|---|---|---|---|---|---|---|---|
| 6 carbon aryl with R² | 6 carbon aryl with R¹ | CH₃ | CH₃ | H | H | F | H | OH | CH₂ | C |
| phenol, 2,2'-[[[(2-hydroxyphenyl)methylene]amino]methyl]-2-methyl-1,3-propanediyl]bis(nitrilomethylidyne)]bis- 3,4,5-trimethoxyphenol, 2,2'-[[[(4,5,6-trimethoxy-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | OCH₃ | OCH₃ | OCH₃ | OH | CH₂ | C |
| 3,5-dimethoxy-4-methyl-phenol, 2,2'-[[[(4,6-dimethoxy-5-methyl-2-hydroxyphenyl)methylene]amino]methyl]-2-methyl-1,3-propanediyl)bis(nitrilomethylidyne)]bis- | | | | | | | | | | |
| 6 carbon aryl with R² | 6 carbon aryl with R¹ | H | CH₃ | H | OCH₃ | CH₃ | OCH₃ | OH | CH₂ | C |
| phenol, 2,2'-[[[(2-hydroxyphenyl)methylene]amino]methyl]-2-methoxyethoxymethyl-1,3-propanediyl]bis(nitrilomethylidyne)]bis- | | | | | | | | | | |
| 6 carbon aryl with R² | 6 carbon aryl with R¹ | H | CH₂O(CH₂)₂OCH₃ | H | H | H | H | OH | CH₂ | C |
| 3,4,5-trimethoxyphenol, 2,2'-[[[(4,5,6-trimethoxy-2-hydroxyphenyl)methylene]amino]methyl]-2-methoxymethyl-1,3-propanediyl]bis(nitrilomethylidyne)]bis- | | | | | | | | | | |
| 6 carbon aryl with R² | 6 carbon aryl with R¹ | H | CH₂—O—CH₃ | H | OCH₃ | OCH₃ | OCH₃ | OH | CH₂ | C |
| 4-methylthiophenol, 2,2'-[[[(5-methylthio-2-hydroxyphenyl)methylene]amino-]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | H | SCH₃ | H | OH | CH₂ | C |
| acetoxymethyl-4-hydroxybenzoate, 3,3'-[[2-[[[(5-carboacetoxymethyl-2-hydroxyphenyl)methylene]amino]methyl]-2-methyl-1,3-propanediyl]-bis(nitrilomethylidyne)]bis- | | | | | | | | | | |
| 6 carbon aryl with R² | 6 carbon aryl with R¹ | H | CH₃ | H | H | O‖COCH₂ | O‖OCCH₃H | OH | CH₂ | C |
| N,N,N-tris[[[[(2-hydroxy-5-methoxyphenyl)methylene]amino]ethyl]amine | | | | | | | | | | |
| 6 carbon aryl with R² | 6 carbon aryl with R¹ | H | — | H | H | OCH₃ | H | OH | (CH₂)₂ | N |
| phenol, 2,2'[[[(2-hydroxyphenyl)methylene]amino]methyl]-2-α-napthoxymethyl-1,3-propanediyl]bis(nitrilomethylidyne)]bis- | | | | | | | | | | |
| 6 carbon aryl with R² | 6 carbon aryl with R¹ | H | CH₂OC₁₀H₇ | H | H | H | H | OH | CH₂ | C |
| 4-methoxyphenol, 2,2'-[[[(5-methoxy-2-hydroxyphenyl)methylene]amino]methyl]-2-α-napthoxymethyl-1,3-propanediyl]bis(nitrilomethylidyne)]bis- | | | | | | | | | | |
| 6 carbon aryl with R² | 6 carbon aryl with R¹ | H | CH₂OC₁₀H₇ | H | H | OCH₃ | H | OH | CH₂ | C |
| 1,3-dihydroxybenzene, 4,4'-[[[2-[[[(2,4-dihydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | OH | H | H | OH | CH₂ | C |
| 1,2-dihydroxybenzene, 3,3'-[[[2-[[[(2,3-dihydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | OH | H | H | H | OH | CH₂ | C |
| 4-(2-methoxy-2-methyl-propyl)phenol, 2,2'-[[[(5-(2-methoxy-2-methyl-propyl)-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | H | CH₂C(CH₃)₂ \| OCH₃ | H | OH | CH₂ | C |
| phenol, 2,2'-[[[(2-hydroxyphenyl)methylene]amino]methyl]-2-phenylmethoxymethyl-1,3-propanediyl]bis(nitrilomethylidyne)]bis- | | | | | | | | | | |
| 6 carbon aryl with R² | 6 carbon aryl with R¹ | H | CH₂OCH₂φ | H | H | H | H | OH | CH₂ | C |
| phenol, 2,2'-[[[(2-hydroxyphenyl)methylene]amino]methyl]-2-octanoyloxymethyl-1,3-propanediyl]bis(nitrilomethylidyne)]bis- | | | | | | | | | | |
| 6 carbon aryl with R² | 6 carbon aryl with R¹ | H | CH₂OCC₇H₁₅ ‖ O | H | H | H | H | OH | CH₂ | C |
| phenol, 2,2'-[[[(2-hydroxyphenyl)isopropoxycarbonyl)methylene]amino]methyl]-2-methyl-1,3-propanediyl]bis(nitrilo(isopropoxycarbonyl)methylidyne)]bis- | | | | | | | | | | |
| 6 carbon aryl with R² | 6 carbon aryl with R¹ | CO₂CH(CH₃)₂ | CH₃ | H | H | H | H | OH | CH₂ | C |
| 4-fluorophenol, 2,2'-[[2-[[[(5-fluoro-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | H | F | H | OH | CH₂ | C |

TABLE 1-continued

| R[1] | R[2] | R[3] | R[4] | R[5] | R[6] | R[7] | R[8] | X | W | Z |
|---|---|---|---|---|---|---|---|---|---|---|
| aryl with R[2] phenol, 2,2'-[[[(2-hydroxyphenyl)methylene]amino]methyl]-2-hydroxymethyl-1,3-propanediyl]bis(nitrilomethylidyne)]bis- 6 carbon | aryl with R[1] | H | CH$_2$OH | H | H | H | H | OH | CH$_2$ | C |
| phenol, 2,2'-[[[(2-hydroxyphenyl)methylene]amino]methyl]-2-methyl-1,3-propanediyl]bis(nitrilopropylidyne)]bis- 6 carbon aryl with R[2] | aryl with R[1] | H | CH$_2$CH$_3$ | H | H | H | OH | H | CH$_2$ | C |
| phenol, 2,2'-[[[(2-hydroxyphenyl)butylene]amino]methyl]-2-methyl-1,3-propanediyl]bis(nitrilobutylidyne)]bis- 6 carbon aryl with R[2] | aryl with R[1] | H | CH$_2$CH$_2$CH$_3$ | H | H | H | OH | H | CH$_2$ | C |
| phenol, 2,2'-[[[(2-hydroxyphenyl)heptylene]amino]methyl]-2-methyl-1,3-propanediyl]bis(nitriloheptylidyne)]bis- 6 carbon aryl with R[2] | aryl with R[1] | H | (CH$_2$)$_5$CH$_3$ | H | H | H | OH | H | CH$_2$ | C |
| 4-hydroxybenzoate, 3,3'-[[[2-[[(5-carboxy-2-hydroxyphenyl)methylene]amino]methyl]-2-methyl-1,3-propanediyl]bis(nitrilomethylidyne)]bis-trisodium salt 6 carbon aryl with R[2] | aryl with R[1] | H | CH$_3$ | H | H | CO$_2$Na | H | H | CH$_2$ | C |
| phenol, 2,2'-[[[(2-hydroxyphenyl)methylene]amino]methyl]-2-propenyloxymethyl-1,3-propanediyl]bis(nitrilomethylidyne)]bis- 6 carbon aryl with R[2] | aryl with R[1] | H | CH$_2$OCH$_2$CHCH$_2$ | H | H | H | H | OH | CH$_2$ | C |
| N-methyl-N,N,N-tris[[[(2-hydroxy-5-methoxyphenyl)methylene]amino]ethyl]ammonium iodide 6 carbon aryl with R[2] | aryl with R[1] | H | CH$_3$ −CH$_2$CH$_2$N(CH$_3$)$_2$ | H | H | OCH$_3$ | H | OH | CH$_2$—CH$_2$ | N[+]I[−] |
| 2-methoxyphenol, 6,6'-[[[2-[[(2-hydroxy-3-methoxyphenyl)methylene]amino]methyl]-2-methyl-1,3-propanediyl]bis(nitrilomethylidyne)]bis- 6 carbon aryl with R[2] | aryl with R[1] | H | CH$_3$ | OCH$_3$ | H | H | H | OH | CH$_2$ | C |
| phenol, 2,2'-[[[(2-hydroxyphenyl)3-N,N-dimethylaminopropylene]amino]methyl]-2-methyl-1,3-propanediyl]bis(nitrilo-3-N,N-dimethylaminopropylidyne)]bis- 6 carbon aryl with R[2] | aryl with R[1] | H | CH$_3$ | H | H | H | H | OH | CH$_2$ | C |
| 4-methoxyphenol, 2,2'-[[[2-[[(2-hydroxy-5-methoxyphenyl)ethylene]amino]methyl]-2-methyl-1,3-propanediyl]bis(nitrilomethylidyne)]bis- 6 carbon aryl with R[2] | aryl with R[1] | H | CH$_3$ | H | H | OCH$_3$ | H | OH | CH$_2$ | C |
| 4-t-butylphenol, 2,2'-[[[(5-t-butyl-2-hydroxyphenyl)methylene]amino]methyl]-2-methyl-1,3-propanediyl]bis(nitrilomethylidyne)]bis- 6 carbon aryl with R[2] | aryl with R[1] | H | CH$_3$ | H | H | t-butyl | H | OH | CH$_2$ | C |
| 4-isopropylphenol, 2,2'-[[[(5-isopropyl-2-hydroxyphenyl)methylene]amino]methyl]-2-methyl-1,3-propanediyl]bis(nitrilomethylidyne)]bis- 6 carbon aryl with R[2] | aryl with R[1] | H | CH$_3$ | H | H | isopropyl | H | OH | CH$_2$ | C |
| 4-ethylphenol, 2,2'-[[[(5-ethyl-2-hydroxyphenyl)methylene]amino]methyl]-2-methyl-1,3-propanediyl]bis(nitrilomethylidyne)]bis- 6 carbon aryl with R[2] | aryl with R[1] | H | CH$_3$ | H | H | CH$_2$CH$_3$ | H | OH | CH$_2$ | C |
| 4-(trimethylammonium)phenol, 2,2'-[[[2-[[(2-hydroxy-5-(trimethylammonium)methylene]amino]methyl]-2-methyl-1,3-propanediyl]bis(nitrilomethylidyne)]bis-triiodide 6 carbon aryl with R[2] | aryl with R[1] | H | CH$_3$ | H | H | N(CH$_3$)$_3$[+]I[−] | H | OH | CH$_2$ | C |
| phenol, 2,2'-[[[(2-hydroxyphenyl)methylene]amino]methyl]-2-phenyl-1,3-propanediyl]bis(nitrilomethylidyne)]bis- 6 carbon aryl with R[2] | aryl with R[1] | H | φ | H | H | H | H | OH | CH$_2$ | C |

TABLE 1-continued

| R¹ | R² | R³ | R⁴ | R⁵ | R⁶ | R⁷ | R⁸ | X | W | Z |
|---|---|---|---|---|---|---|---|---|---|---|
| phenol, 2,2'-[[[(2-hydroxyphenyl)methylene]amino]methyl]-2-phenoxymethyl-1,3-propanediyl]bis(nitrilomethylidyne)]bis- | | | | | | | | | | |
| 6 carbon aryl with R² | 6 carbon aryl with R¹ | H | CH₂Oφ | H | H | H | H | OH | CH₂ | C |
| 2-ethylphenol, 6,6'-[[[(3-ethyl-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | —CH₂CH₃ | H | H | H | OH | CH₂ | C |
| 3,4,5-trimethoxyphenol, 2,2'-[[[(4,5,6-trimethoxy-2-hydroxyphenyl)methylene]amino]methyl]-2-phenylmethoxymethyl-1,3-propanediyl]bis(nitrilomethylidyne)]bis- | | | | | | | | | | |
| 6 carbon aryl with R² | 6 carbon aryl with R¹ | H | CH₂OCH₂φ | H | OCH₃ | OCH₃ | OCH₃ | OH | CH₂ | C |
| 3,4,5-trimethoxyphenol, 2,2'-[[[(4,5,6-trimethoxy-2-hydroxyphenyl)methylene]amino]methyl]-2-(4-methoxyphenyl)methoxymethyl-1,3-propanediyl]bis(nitrilomethylidyne)]bis- | | | | | | | | | | |
| 6 carbon aryl with R² | 6 carbon aryl with R¹ | H | CH₂OCH₂(4-MeOC₆H₄) | H | OCH₃ | OCH₃ | OCH₃ | OH | CH₂ | C |
| 3,4,5-trimethoxyphenol, 2,2'-[[[(4,5,6-trimethoxy-2-hydroxyphenyl)methylene]amino]methyl]- 2-(3,4,5-trimethoxyphenyl)methoxymethyl-1,3-propanediyl]bis(nitrilomethylidyne)]bis- | | | | | | | | | | |
| 6 carbon aryl with R² | 6 carbon aryl with R¹ | H | CH₂OCH₂(3,4,5,-MeOC₆H₂) | H | OCH₃ | OCH₃ | OCH₃ | OH | CH₂ | C |
| phenol, 2,2'-[[[(4,5,6-trimethoxy-2-hydroxyphenyl)methylene]amino]methyl]-2-(3,4,5-trimethoxyphenyl)methoxymethyl-1,3-propanediyl]bis(nitrilomethylidyne)]bis- | | | | | | | | | | |
| 6 carbon aryl with R² | 6 carbon aryl with R¹ | H | CH₂OCH₂(3,4,5,-MeOC₆H₂) | H | H | H | H | OH | CH₂ | C |
| phenol, 2,2'-[[[(2-hydroxyphenyl)methoxymethyl]-2-(4-methoxyphenyl)methoxymethyl-1,3-propanediyl]bis(nitrilomethylidyne)]bis- | | | | | | | | | | |
| 6 carbon aryl with R² | 6 carbon aryl with R¹ | H | CH₂OCH₂(4-MeOC₆H₄) | H | H | H | H | OH | CH₂ | C |
| tris(2-salicylideneiminoethyl)amine | | | | | | | | | | |
| 6 carbon aryl with R² | 6 carbon aryl with R¹ | H | — | H | H | H | H | OH | (CH₂)₂ | N |
| phenol, 2,2'-[[[(2-hydroxyphenyl)methylene]amino]methyl]-2-(4-methoxy-4-methyl)pentyl-1,3-propanediyl]bis(nitrilomethylidyne)]bis- | | | | | | | | | | |
| 6 carbon aryl with R² | 6 carbon aryl with R¹ | H | (CH₂)₃CH(OCH₃)CH₃ CH₃ | H | H | H | OH | CH₃ | CH₂ | C |
| 4-fluorophenol, 2,2'-[[[(5-fluoro-2-hydroxyphenyl)methylene]amino]methyl]-2-phenylmethoxymethyl-1,3-propanediyl]bis(nitrilomethylidyne)]bis- | | | | | | | | | | |
| 6 carbon aryl with R² | 6 carbon aryl with R¹ | H | CH₂OCH₂φ | H | H | F | H | OH | CH₂ | C |
| 4-hydroxybenzenesulfonic acid, 3,3'-[[2-[[[(5-sulfo-2-hydroxyphenyl)methylene]amino]methyl]-2-methyl-1,3-propanediyl]bis(nitrilomethylidyne)]bis-trisodium salt | | | | | | | | | | |
| 6 carbon aryl with R² | 6 carbon aryl with R¹ | H | CH₃ | H | H | SO₃⁻Na⁺ | H | OH | CH₂ | C |
| 2,4-difluorophenol, 2,2'-[[2-[[[(3,5-difluoro-2-hydroxyphenyl)methylene]amino]methyl]-2-phenylmethoxymethyl-1,3-propanediyl]bis(nitrilomethylidyne)]bis- | | | | | | | | | | |
| 6 carbon aryl with R² | 6 carbon aryl with R¹ | H | CH₂OCH₂φ | F | H | F | H | OH | CH₂ | C |
| 2-naphthol, 1,1'-[[2-[[[(2-hydroxynaphthyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | H | together w/R7 form 6C aryl | together w/R8 form 6C aryl | OH | CH₂ | C |
| 4-bromophenol, 2,2'-[[2-[[[(5-bromo-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | H | Br | H | OH | CH₂ | C |
| 4-chlorophenol, 2,2'[[2-[[[(5-chloro-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | H | Cl | H | OH | CH₂ | C |
| 3,5-Dimethyl-4-methoxyphenol, 2,2'-[[2-[[[(4,6-dimethyl-5-methoxy-2-hydroxyphenyl)-methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | CH₃ | OCH₃ | CH₃ | OH | CH₂ | C |
| 4-(trifluoromethyl)phenol, 2,2'-[[2-[[[(5-trifluoromethyl)-2-hydroxyphenyl)methylene]amino]methyl]-2-methyl-1,3-propanediyl]bis(nitrilomethylidyne)]bis- | | | | | | | | | | |

TABLE I-continued

| R¹ | R² | R³ | R⁴ | R⁵ | R⁶ | R⁷ | R⁸ | X | W | Z |
|---|---|---|---|---|---|---|---|---|---|---|
| 6 carbon aryl with R² | 6 carbon aryl with R¹ | H | CH₃ | H | H | CF₃ | H | OH | CH₂ | C |
| 4-Methoxyphenyl, 2,2'-[[2-[[[(5-methoxy-2-hydroxyphenyl)methylene]amino]methyl]-2-propoxymethyl-1,3-propanediyl]bis(nitrilomethylidyne)]bis-| | | | | | | | | | |
| 6 carbon aryl with R² | 6 carbon aryl with R¹ | H | CH₂—O—(CH₂)₂CH₃ | H | H | OCH₃ | H | OH | CH₂ | C |
| Phenol, 2,2'-[[2-[[[(2-hydroxyphenyl)methylene]amino]methyl]-2-methoxypropyl-1,3-propanediyl]bis(nitrilomethylidyne)]bis- | | | | | | | | | | |
| 6 carbon aryl with R² | 6 carbon aryl with R¹ | H | CH₂—(CH₂)₂OCH₃ | H | H | H | H | OH | CH₂ | C |
| Phenol, 2,2'-[[[2-[[[(2-hydroxyphenyl)methylene]amino]methyl]-2-(2-methylpropoxy)methyl-1,3-propanediyl]bis(nitrilomethylidyne)]- | | | | | | | | | | |
| 6 carbon aryl with R² | 6 carbon aryl with R¹ | H | CH₂OCH₂CH(CH₃)₂ | H | H | H | H | OH | CH₂ | C |
| Phenol, 2,2'-[[[(2-hydroxyphenyl)methylene]amino]methyl]-2-butoxymethyl-1,3-propanediyl]]bis(nitrilomethylidyne)]bis- | | | | | | | | | | |
| 6 carbon aryl with R² | 6 carbon aryl with R¹ | H | CH₂O—(CH₂)₃CH₃ | H | H | H | H | OH | CH₂ | C |
| Phenol, 2,2'-[[2-[[[(2-hydroxyphenyl)methylene]amino]methyl]-2-pentyl-1,3-propanediyl]bis(nitrilomethylidyne)]bis- | | | | | | | | | | |
| 6 carbon aryl with R² | 6 carbon aryl with R¹ | H | CH₂—(CH₂)₃CH₃ | H | H | H | H | OH | CH₂ | C |
| Phenol, 2,2'-[[[2-[[[(2-hydroxyphenyl)methylene]amino]methyl]-2-pentyloxymethyl-1,3-propandiyl]bis(nitrilomethylidyne)]bis- | | | | | | | | | | |
| 6 carbon aryl with R² | 6 carbon aryl with R¹ | H | CH₂—O—(CH₂)₄CH₃ | H | H | H | H | OH | CH₂ | C |
| Phenol, 2,2'-[[[2-[[[(2-hydroxyphenyl)methylene]amino]methyl]-2-(1-methylethoxy)methyl-1,3-propanediyl]bis(nitrilomethylidyne)]bis- | | | | | | | | | | |
| 6 carbon aryl with R² | 6 carbon aryl with R¹ | H | CH₂OCH(CH₃)₂ | H | H | H | H | OH | CH₂ | C |
| Phenol, 2,2'-[[2-[[[(2-hydroxyphenyl)methylene]amino]methyl]-(1-methylpropoxy)methyl-1,3-propanediyl]bis(nitrilomethylidyne)]bis- | | | | | | | | | | |
| 6 carbon aryl with R² | 6 carbon aryl with R¹ | H | CH₂OCH(CH₃)CH₂CH₃ | H | H | H | H | OH | CH₂ | C |
| 3-Methylphenol, 6,6'-[[2-[[[(4-methyl-2-hydroxyphenyl)methylene]amino]methyl]-2-propoxymethyl-1,3-propanediyl]bis(nitrilomethylidyne)]bis- | | | | | | | | | | |
| 6 carbon aryl with R² | 6 carbon aryl with R¹ | H | CH₂O(CH₂)₂CH₃ | H | CH₃ | H | H | OH | CH₂ | C |
| 3-Methylphenol, 6,6'-[[2-[[[(4-methyl-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | CH₃ | H | H | OH | CH₂ | C |
| 3-Methylthiophenol, 6,6'-[[2-[[[(4-methylthio-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | SCH₃ | H | H | OH | CH₂ | C |
| 3-Dimethylaminophenol, 6,6'-[[2-[[[(4-dimethylamino-2-hydroxy-phenyl)methylene]amino]methyl]-2-methyl-1,3-propanediyl]bis-(nitrilomethylidyne)]bis- | | | | | | | | | | |
| 6 carbon aryl with R² | 6 carbon aryl with R¹ | H | CH₃ | H | N(CH₃)₂ | H | H | OH | CH₂ | C |
| 3-Methoxyphenol, 6,6'-[[2-[[[(4-methoxy-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | OCH₃ | H | H | OH | CH₂ | C |
| 3-Methoxyphenol, 2,2'-[[2-[[[(6-methoxy-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | CH₃ | H | OCH₃ | OH | CH₂ | C |
| 3-Ethoxyphenol, 6,6'-[[2-[[[(4-ethoxy-2-hydroxyphenyl)methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | OCH₂CH₃ | H | H | OH | CH₂ | C |
| Phenol, 2,2'-[[[2-[[[(5-tert-octyl-2-hydroxyphenyl)-methylene]amino]methyl]-2-methyl-1,3-propanediyl]bis(nitrilomethylidyne)]bis- | | | | | | | | | | |
| 6 carbon aryl with R² | 6 carbon aryl with R¹ | H | CH₃ | H | H | C(CH₃)₂CH₂C(CH₃)₃ | H | OH | CH₂ | C |

EXAMPLE 95

Eluate from a Mo/Tc generator containing $^{99m}$Tc was taken to dryness in vacuo and diluted with 50 ml ethanol. This ethanol mixture was taken to dryness and the ethanol addition and drying repeated. The resulting solid was extracted with 10 ml of ethanol giving about 60 mCi per ml. Two ml of this solution were mixed by sonication with 5 mg of (sal)$_3$tame O-n-propyl

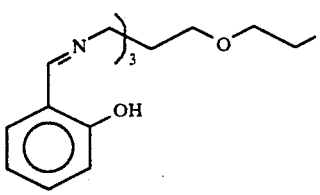

in a 10 ml serum vial and 60 μL of SnCL$_2$ solution (7 mg of SnCl$_2$. 2H$_2$O per ml of EtOH) were added. The vial was capped with a teflon coated stopper, crimp sealed with an aluminum cap, heated to 100° C. and maintained at that temperature for 30 min. The reaction mixture was cooled and 0.5 ml of reaction mixture was mixed with 1 ml of 90/10 H$_2$O/EtOH, 0.1% HOAc. After filtering through a 0.2 μm filter, the clear filtrate was purified by HPLC using a C-4 column (Macrosphere 250×4.6 mm, 7 μ) with a gradient elution using 90/10 H$_2$O/EtOH (0.1% HOAC) (solvent A) and 10/90 H$_2$O/EtOH (0.1% acetic acid) (solvent B); 0-6 minutes 100% A, 6-10 minutes from initial to 70% A to 30% B (linear), 10-70 minutes from 70/30 to 0/100 (linear gradient). The peak at 41.8 minutes was collected. The radiochemical yield of the preparation was 84% and the final purity was 95% using paper chromatography (both saline and MeOH development).

EXAMPLE 96

One ml of Na$^{99m}$TcO$_4$ in ethanol was treated with 2 mg of 1,1,1-tris(2-hydroxyphenylmethylaminomethyl)-2-propoxyethane,

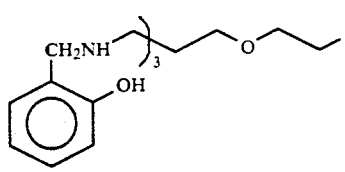

and after sonication to dissolve the ligand, 140 μg of SnCl$_2$.2H$_2$O was added. The reaction vial was then sealed and heated at 100° C. for 30 minutes. After cooling the reaction mixture to room temperature, 0.25 ml was added to 1 ml of 95/5 H$_2$O/EtOH. The resulting cloudy solution was then passed through a 0.2 μm filter, and the clear filtrate was then purified by HPLC using a PRP-1 column (250×4.1 mm, 10 μ) with a gradient elution using 95/5 H$_2$O/EtOH (solvent A) and 100% EtOH (0.05% acetic acid) (Solvent B); 0-25 minutes from 100% A to 100% B (curve #5 gradient). The peak at 15.6 min was collected. The product was 88% pure by paper chromatography.

This complex was shown using HPLC, paper chromatography, guinea pig biodistributions and mass spectrum evaluation of the $^{99}$Tc level preparation to be identical to the complex formed as above (Example 95) using (sal)$_3$tame-O-n-propyl.

EXAMPLE 97

2.0 ml Na$^{99m}$TcO$_4$ reconstituted as in example 95 was used to dissolve 3 mg of (5-methylsal)$_3$ tame.

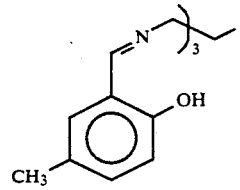

To this was added 40 μL of SnCl$_2$ solution (see example 75) and the mixture sealed and heated at 100° C. for 30 minutes. The reaction mixture was combined with twice the volume of water and the mixture allowed to precipitate. The mixture was filtered through a 0.2 μm filter and purified by HPLC using a Hamilton PRP-1 column, 250×4.1 mm, 10μ. A gradient was run using 95/5 water/ethanol (solvent A) and ethanol with 0.1% acetic acid (solvent B) in which the percentage of solvent B increased linearly from 0 to 100% over the first 30 minutes of the run. Pure solvent B then was held during the last twenty minutes of the run. The peak was collected that eluted at 30.9 minutes (flow=1.0 ml/min). The radiochemical yield was 76% and the radiochemical purity was >92% by paper chromatography.

EXAMPLE 98

Two ml of Na$^{99m}$TcO$_4$ in ethanol was treated with 3 mg of (4,6-dimethoxysal)$_3$tame

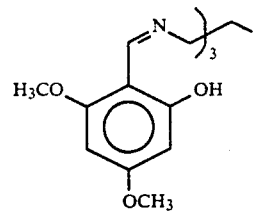

and, after sonication, with 140 μg of SnCl$_2$. 2H$_2$O. The mixture was heated at 100° C. for 30 minutes. After dilution of the reaction mixture 1:2 with water and filtering through a 0.2 μm filter the material was purified by HPLC using the gradient in example 97 with the major peak, (38.6 min, 78%) collected. The product was 92% pure by paper chromatography.

EXAMPLE 99

One ml of Na$^{99m}$TcO$_4$ in ethanol was treated with 3 mg of (4-MeOsal)$_3$tame 0-n-propyl

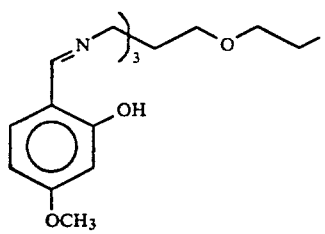

and after sonication to dissolve the ligand, 140 μg of SnCl$_2$.2H$_2$O was added and the reaction vial sealed and heated at 100° C. for 30 minutes. The reaction mixture was diluted 1:2 with water and filtered through a 0.2 μm filter. The product was purified by HPLC using the conditions in example 97. The product was 92% pure by paper chromatography.

EXAMPLE 100

One ml of Na$^{99m}$TcO$_4$ in ethanol was treated with 3mg of (4-methylsal)$_3$tame

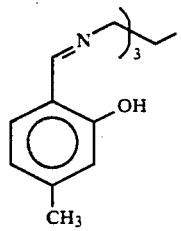

and after sonication to dissolve the ligand, 140 μg of SnCl$_2$.2H$_2$O was added and the reaction vial sealed and heated at 100° C. for 30 minutes. The reaction mixture was diluted 1:2 with water and filtered through a 0.2 μm filter. The product was purified by HPLC using the conditions in example 97. The product was 88% pure by paper chromatography.

EXAMPLE 101

The Tc-99 complex of (sal)$_3$ tame O-n-propyl was synthesized by an approach similar to that used for the Tc-99m material. A solution of 0.5 mg Na$^{99}$TcO$_4$ in saline was taken to dryness in vacuo. This solid was dissolved in 2.0 ml of Na$^{99m}$TcO$_4$ in ethanol and 5 mg of (sal)$_3$tame O-n-propyl was dissolved in the solution by sonication. This solution was treated with 0.1 ml of SnCl$_2$ solution (see example 95) and the vial sealed and heated at 100° C. for 30 minutes. The color of the solution, which was red-brown on addition of the tin solution changed to violet upon heating. The resulting reaction solution was diluted with 20 ml of water, allowed to stand for 5 minutes, filtered through a 0.2 μm filter and the supernatant loaded onto a Sephadex SP C-25 cation exchange column (Na+ form) which was washed with water and ethanol/water. The violet band was eluted with 0.2 M NaCl. This band was taken to dryness in vacuo and the violet colored NaCl was extracted with ethanol to give a violet solution which was filtered to remove the excess NaCl (reaction yield ca. 80%). The solution was tested using fast-atom bombardment mass spectrometry and the mass of the major peak over 500 mass units was 583, which corresponds to the complex of one technetium and one ligand with the phenolic oxygens on the ligands being deprotonated. This complex must be positively charged as an entity to give a mass spectrum. All the above data indicate that the compound is inherently positively charged. The identical natures of the Tc-99 and Tc-99m complexes were ascertained by coinjecting them on the HPLC and finding that the radiometric and UV peaks coeluted.

EXAMPLE 102

The Tc-99 complex of (5-methylsal)$_3$tame was synthesized in a manner similar to $^{99}$Tc-sal$_3$tame O-n-propyl. Five milligrams of Na$^{99}$TcO$_4$ in water was taken to dryness and treated with two ml of ethanol containing Na$^{99m}$TcO$_4$ and 10 ml of ethanol. Addition of 25 mg of (5-methylsal)$_3$tame followed by sonication produced a yellow solution. Addition of 200 μL of SnCl$_2$ solution (see example 95) produced a red-brown solution that turned violet upon heating at 100° C. for 30 minutes. Rotary evaporation of the product followed by ion-exchange chromatography and removal of the water and extraction with ethanol yielded a violet product in 82% yield. This material was injected onto an HPLC and the UV and radiometric traces were found to be coincident and equivalent to the Tc-99m compound described in example 97.

EXAMPLE 103

The biodistribution of the radionuclide in a body will depend on the ligand and the radionuclide used. The procedures used for determining biodistribution are as follows.

Rats—The technetium complex is injected in restrained but unanesthetized rats. After 5 minutes the rats are sacrificed by cervical dislocation and ca. 2 ml of blood is withdrawn by heart puncture. The animal then is opened and the organs (kidneys, liver, lung, heart and muscle) removed and washed with normal saline, dried, weighed and counted, along with appropriate standards, on a gamma radiation counter.

Guinea Pigs—The guinea pigs are anesthetized and the technetium complex is injected into the jugular vein after a cutdown. The animals are sacrificed after 5 minutes and the organs removed and counted as with the rats.

Dogs—Anesthetized dogs are imaged after paw or tongue vein injection using a planar gamma imager.

In rats, significant heart uptake is determined if the percentage of technetium in the heart is greater than 0.8% and the heart/blood ratio is greater than 1. For guinea pigs, significant heart uptake is determined if the percentage of technetium in the heart is greater than 0.5% and the heart/blood ratio is greater than 1. In dogs, significant heart uptake is determined if the heart muscle is visible after 5 minutes in a planar imager. The imager generally used employs a sodium iodide crystal and produces computer generated images.

The results of tests on the biodistribution in guinea pigs and rats of the ligand-Tc-99m complexes of this invention are shown in Tables II–IV. The heart uptake for each complex tested, measured as the percentage of technetium in the hearts of guinea pigs or rats is given in Tables II and III, respectively. For each of the complexes tested, the heart/blood ratio was found to be greater than 1. The actual ratio for each of four of the ligand-Tc complexes is set forth in Table IV.

TABLE II

Table of Tc Complexes of Sal3 Tame Ligands and Their Biodistributions in Guinea Pigs $$\text{structure: } R^8, R^7, R^6, R^5 \text{ substituted salicylaldehyde with } R^3\text{=N-(CH}_2\text{)}_3\text{-R}^4, \text{OH}$$

| $R^5$ | $R^6$ | $R^7$ | $R^8$ | $R^3$ | $R^4$ | 5 Minute Guinea Pig % HT Uptake |
|---|---|---|---|---|---|---|
| H | H | —CO$_2$CH$_3$ | H | H | CH$_3$ | 1.23 |
| H | OCH$_3$ | H | OCH$_3$ | H | CH$_3$ | 1.71 |
| OCH$_2$CH$_3$ | H | H | H | H | CH$_3$ | 0.50 |
| H | OCH$_3$ | OCH$_3$ | OCH$_3$ | H | CH$_3$ | 1.57 |
| H | H | SCH$_3$ | H | H | CH$_3$ | 1.23 |
| H | OCH$_3$ | CH$_3$ | OCH$_3$ | H | CH$_3$ | 0.84 |
| H | CH$_3$ | OCH$_3$ | CH$_3$ | H | CH$_3$ | 1.07 |
| H | OCH$_3$ | OCH$_3$ | OCH$_3$ | H | CH$_2$OCH$_3$ | 0.86 |
| H | H | H | H | H | CH$_2$OCH$_2$C$_6$H$_5$ | 1.60 |
| H | H | H | H | H | CH$_2$OC(O)(CH$_2$)$_6$CH$_3$ | 0.88 |
| OCH$_3$ | OCH$_3$ | OCH$_3$ | OCH$_3$ | H | CH$_3$ | 1.24 |
| H | OCH$_3$ | OCH$_3$ | OCH$_3$ | H | CH$_2$OCH$_2$C$_6$H$_5$ | 0.60 |
| H | H | H | H | CH$_2$CH$_3$ | CH$_3$ | 0.76 |
| H | H | H | H | H | CH$_2$OCH$_2$(3,4,5-(MeO)$_3$C$_6$H$_2$) | 1.00 |
| H | OCH$_3$ | OCH$_3$ | OCH$_3$ | H | CH$_2$OCH$_2$(4-MeOC$_6$H$_4$) | 1.04 |
| H | OCH$_3$ | OCH$_3$ | OCH$_3$ | H | CH$_2$OCH$_2$(3,4,5-MeOC$_6$H$_2$) | 0.98 |
| H | H | H | H | H | CH$_2$OCH$_2$(4-MeOC$_6$H$_4$) | 1.08 |
| H | H | H | H | H | CH$_2$OCH$_2$CH$_2$CH$_3$ | 1.48 |
| H | H | F | H | CH$_3$ | CH$_3$ | 0.66 |
| H | H | H | H | H | CH$_2$O-(1-napthyl) | 0.72 |
| H | H | CH$_2$C(CH$_3$)$_2$OCH$_3$ | H | H | CH$_3$ | 0.49 |
| H | H | CF$_3$ | H | H | CH$_3$ | 0.51 |
| H | H | F | H | H | CH$_3$ | 1.30 |
| H | H | H | H | H | (CH$_2$)$_2$C(CH$_3$)$_2$OCH$_3$ | 1.61 |
| H | H | H | H | H | H | 1.29 |
| H | H | F | H | H | CH$_2$OCH$_2$C$_6$H$_5$ | 1.14 |
| F | H | F | H | H | CH$_2$OCH$_2$C$_6$H$_5$ | 1.72 |
| H | H | H | H | H | CH$_2$OCH$_2$CH=CH$_2$ | 1.09 |
| H | H | H | H | H | CH$_2$OCH$_3$ | 1.44 |
| H | H | H | H | H | CH$_2$O(CH$_2$)$_5$CH$_3$ | 1.19 |
| H | H | H | H | H | CH$_2$OCH$_2$CH$_2$OCH$_3$ | 1.01 |
| H | H | H | H | H | CH$_2$OCH$_2$CH$_3$ | 1.71 |
| H | H | OCH$_3$ | H | H | CH$_2$OCH$_2$CH$_2$CH$_3$ | 1.52 |
| H | OCH$_3$ | H | OCH$_3$ | H | CH$_2$OCH$_2$CH$_2$CH$_3$ | 1.21 |
| H | H | H | H | H | (CH$_2$)$_4$OCH$_3$ | 1.66 |
| H | H | H | H | H | CH$_2$OCH$_2$CH(CH$_3$)$_2$ | 1.72 |
| H | OCH$_3$ | H | H | H | CH$_2$OCH$_2$CH$_2$CH$_3$ | 0.87 |
| H | H | H | H | H | CH$_2$O(CH$_2$)$_3$CH$_3$ | 1.46 |
| H | H | H | H | H | (CH$_2$)$_4$CH$_3$ | 1.15 |
| H | H | H | H | H | CH$_2$O(CH$_2$)$_4$CH$_3$ | 1.22 |
| H | H | H | H | H | CH2OCH(CH$_4$)$_2$ | 0.57 |
| H | H | CH$_3$ | H | H | CH$_3$ | 1.82 |
| H | H | H | H | H | CH$_2$OCH(CH$_3$)CH$_2$CH$_3$ | 1.55 |
| H | CH$_3$ | H | H | H | CH$_2$OCH$_2$CH$_2$CH$_3$ | 1.79 |
| CH$_2$CH$_3$ | H | H | H | H | CH$_3$ | 0.47 |
| H | CH$_3$ | H | H | H | CH$_3$ | 1.51 |
| H | SCH$_3$ | H | H | H | CH$_3$ | 1.72 |
| H | N(CH$_3$)$_2$ | H | H | H | CH$_3$ | 0.72 |
| H | OCH$_3$ | H | H | H | CH$_3$ | 2.11 |
| H | H | H | OCH$_3$ | H | CH$_3$ | 1.55 |
| H | OCH$_2$CH$_3$ | H | H | H | CH$_3$ | 0.98 | structure: $R^8, R^7, R^6, R^5$ substituted with $R^3$=N-(CH$_2$)$_3$-N, OH

| $R^5$ | $R^6$ | $R^7$ | $R^8$ | $R^3$ | $R^4$ | |
|---|---|---|---|---|---|---|
| H | H | H | H | H | — | 0.84 |

TABLE III

Table of Tc Complexes of Sal3 Tame Ligands and Their Biodistributions in Rats

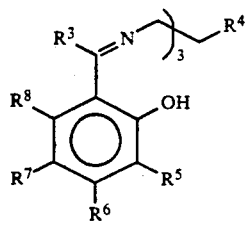

| R⁵ | R⁶ | R⁷ | R⁸ | R³ | R⁴ | 5 Minute Rat Bio distribution % HT Uptake |
|---|---|---|---|---|---|---|
| H | H | H | H | H | H | 1.75 |
| H | H | — | H | H | H | 1.31 |
| H | H | OCH₃ | H | H | H | 1.31 |
| H | H | —O—C₆H₄ | — | H | H | 1.51 |
| H | H | (CH₃)₂CH— | H | H | H | 0.81 |
| H | H | (CH₃)₃C— | H | H | H | 0.91 |
| H | H | C(CH₃)₂CH₂C(CH₃)₃ | H | H | H | 1.27 |
| H | H | —NO₂ | H | H | H | 1.14 |

TABLE IV

Ligand

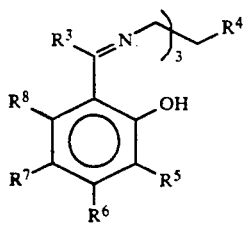

| R⁵ | R⁶ | R⁷ | R⁸ | R³ | R⁴ | Guinea Pig Heart/ Blood Ratio |
|---|---|---|---|---|---|---|
| H | OCH₃ | H | OCH₃ | H | CH₃ | 12 |
| H | H | CH₃ | H | H | CH₃ | 18 |
| H | OCH₃ | H | H | H | CH₃ | 16 |

TABLE IV-continued

Ligand

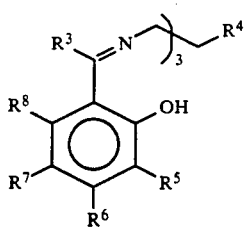

| R⁵ | R⁶ | R⁷ | R⁸ | R³ | R⁴ | Guinea Pig Heart/ Blood Ratio |
|---|---|---|---|---|---|---|
| H | H | H | H | H | CH₂—O—(CH₂)₂CH₃ | 18 |

We claim:

1. A complex useful as a radiopharmaceutical imaging agent comprising technetium in the +4 oxidation state bonded to a ligand having the formula:

wherein
Z is C, and the three Y groups are characterized by the general formula.

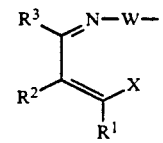

wherein
R¹ and R² taken together with the carbon atoms to which they are directly attached, form an aryl group, R³ is H, R⁴ is CH₂OCH₂CH₂CH₃, each of R⁵, R⁶, R⁷, and R⁸ is H and W is CH₂ such that y has the general formula

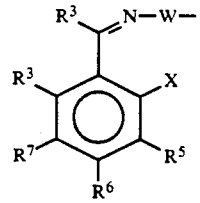

wherein
X is OH.

* * * * *